United States Patent
Yamada et al.

(10) Patent No.: US 8,339,617 B2
(45) Date of Patent: Dec. 25, 2012

(54) FILM THICKNESS MEASURING DEVICE AND FILM THICKNESS MEASURING METHOD

(75) Inventors: Takeo Yamada, Tokyo (JP); Takeshi Yamamoto, Tokyo (JP); Takahiro Yamakura, Tokyo (JP); Shinji Hayashi, Tokyo (JP); Shingo Kawai, Tokyo (JP)

(73) Assignee: Nireco Corporation, Tokyo (JP)

( * ) Notice: Subject to any disclaimer, the term of this patent is extended or adjusted under 35 U.S.C. 154(b) by 181 days.

(21) Appl. No.: 12/904,494

(22) Filed: Oct. 14, 2010

(65) Prior Publication Data

US 2011/0032541 A1  Feb. 10, 2011

Related U.S. Application Data

(63) Continuation of application No. PCT/JP2009/003507, filed on Jul. 24, 2009.

(30) Foreign Application Priority Data

Jul. 30, 2008  (JP) .................... PCT/JP2008/063679

(51) Int. Cl.
*G01B 11/28* (2006.01)
*G01N 21/25* (2006.01)
(52) U.S. Cl. ........................................ 356/630; 356/405
(58) Field of Classification Search .................. 356/630, 356/632, 503, 504
See application file for complete search history.

(56) References Cited

U.S. PATENT DOCUMENTS

| | | | |
|---|---|---|---|
| 4,899,055 A * | 2/1990 | Adams | 250/372 |
| 5,087,121 A * | 2/1992 | Kakuchi et al. | 356/73 |
| 2004/0070773 A1 | 4/2004 | Hirose et al. | |
| 2005/0094160 A1 * | 5/2005 | Murai et al. | 356/630 |
| 2007/0055951 A1 | 3/2007 | Hayashi et al. | |
| 2008/0049222 A1 | 2/2008 | Yamaguchi et al. | |

FOREIGN PATENT DOCUMENTS

| | | |
|---|---|---|
| JP | 7-141703 | 6/1995 |
| JP | 9-73667 | 3/1997 |
| JP | 2005-249602 | 9/2005 |
| JP | 2008-76379 | 4/2008 |

OTHER PUBLICATIONS

Chinese Office Action application No. 200980111320.1 dated Aug. 10, 2011.

* cited by examiner

*Primary Examiner* — Gregory J Toatley
*Assistant Examiner* — Hina F Ayub
(74) *Attorney, Agent, or Firm* — Squire Sanders (US) LLP

(57) ABSTRACT

A film thickness measuring device is provided with a light source, a spectroscopic sensor, a processor, and a storage unit, and configured in such a manner that light from the light source vertically enters a plane to be measured provided with a film and the light reflected by the plane to be measured enters the spectroscopic sensor. The storage unit stores theoretical values of reflectivity distributions of respective film thicknesses and theoretical values of color characteristic variables of the respective film thicknesses. The processor finds the thickness of the film of the plane to be measured from the reflectivity distribution measured by the spectroscopic sensor by using the theoretical values of the reflectivity distributions of the respective film thicknesses or the theoretical values of the color characteristic variables of the respective film thicknesses stored in the storage unit.

7 Claims, 28 Drawing Sheets

FILM THICKNESS MEASURING DEVICE AND FILM THICKNESS MEASURING METHOD

TECHNICAL FIELD

The present invention relates to a film thickness measuring device and a film thickness measuring method for obtaining a thickness of a film formed on a substrate by measuring spectral reflectivity.

BACKGROUND ART

For measuring a thickness of a film formed on a substrate, there exist an ellipsometer (which is disclosed in Japanese Patent Application Laid Open No. 2009-68937, for example) and a measuring device in which a film thickness is obtained from the wavelength which shows maximum or minimum in spectral reflectivity (which is hereinafter referred to as a PV (Peak-Valley) device and disclosed in Japanese Patent No. 3532165, for example).

The ellipsometer is widely used for measurement of a thin film thickness in the field of manufacturing semiconductors. However, the ellipsometer has the following problems. Since the projection angle and the receiving angle are large, the ellipsometer can hardly be used in a process in which a distance to the object will change. Since optical elements both on the projection and receiving sides have to be rotated for the measurement, the optical system is complicated and expensive.

Since, in the PV device, a film thickness is obtained from the wavelength which shows maximum or minimum in spectral reflectivity, it is necessary that the wavelength which shows maximum or minimum in spectral reflectivity should exist. However, in general, in spectral reflectivity data of thin films thickness of which is 500 nm or less, the wavelength which clearly shows maximum or minimum will not exist. Accordingly, the conventional PV device cannot be used for measurement of thin films thickness of which is 500 nm or less.

SUMMARY OF INVENTION

Problems to be Solved by the Invention

Thus, there is a need for a film thickness measuring device of a simple structure and a film thickness measuring method which can be used for thin films thickness of which is 500 nm or less.

Means for Solving the Problem

A film thickness measuring device according to the present invention includes a light source, a spectroscopic sensor, a processor, and a memory, and the device is configured such that light from the light source is perpendicularly incident on an object surface with a film and light reflected by the object surface is led to enter the spectroscopic sensor. The memory stores theoretical values of reflectivity distribution for each film thickness and theoretical values of a characteristic variable for each film thickness, and the processor obtains a film thickness of the film of the object surface based on a reflectivity distribution measured by the spectroscopic sensor using the theoretical values of reflectivity distribution for each film thickness or the theoretical values of the characteristic variable for each film thickness stored in the memory.

In the film thickness measuring device according to the present invention, a film thickness of the film of the object surface is obtained based on a reflectivity distribution measured by the spectroscopic sensor using the theoretical values of reflectivity distribution for each film thickness or the theoretical values of the characteristic variable for each film thickness. Accordingly, a film thickness can be obtained even when a wavelength corresponding to a maximum value or a minimum value does not apparently exist in the reflectivity distribution. As a result, the film thickness measuring device according to the present invention can be used for a thin film of 500 nm or less.

A film thickness measuring device according to an embodiment of the present invention further includes a beam splitter and the device is configured such that during a measurement period, light from the light source passes through the beam splitter and is perpendicularly incident on the object surface and light reflected by the object surface travels in a direction perpendicular to the object surface, passes through the beam splitter and reaches the spectroscopic sensor.

In the film thickness measuring device according to the present embodiment, by the use of a beam splitter, the device can be configured such that light from the light source is perpendicularly incident on the object surface and then light reflected by the object surface in a direction perpendicular to the object surface is led to the spectroscopic sensor. Accordingly, when a thin film is formed on the object surface, the film thickness measuring device according to the present embodiment is able to carry out measurement of multi-reflection caused by the thin film, and therefore accuracy in measurement of reflectivity can be improved.

A film thickness measuring device according to another embodiment of the present invention further includes a hollow member for correcting reflectivity zero point with an aperture and a reflectivity correcting plate and the device is configured such that during a period for correcting reflectivity zero point, light from the light source passes through the beam splitter and enters the aperture of the hollow member for correcting reflectivity zero point and light reflected by the hollow member travels in a direction perpendicular to the object surface, passes through the beam splitter and reaches the spectroscopic sensor. The film thickness measuring device according to the present embodiment is configured such that during a period for calibrating reflectivity, light from the light source passes through the beam splitter and is perpendicularly incident on the reflectivity correcting plate and light reflected by the reflectivity correcting plate travels in a direction perpendicular to the reflectivity correcting plate, passes through the beam splitter and reaches the spectroscopic sensor. The memory stores reflectivity of the reflectivity correcting plate Rv(Ref) and the processor obtains reflectivity of the object surface Rv(T) using equation $$Rv(T)=Rv(\text{Ref})\cdot(V(M)-V(D))/(V(C)-V(D))$$

where V(M) represents output of the spectroscopic sensor during the measurement period, V(D) represents output of the spectroscopic sensor during the period for correcting reflectivity zero point, and V(C) represents output of the spectroscopic sensor during the period for calibrating reflectivity.

In the film thickness measuring device according to the present embodiment, a portion of input of the spectroscopic sensor generated by lights besides light reflected by the object surface can be removed, and therefore a reflectivity distribution of the object surface can be measured with a higher accuracy.

In a film thickness measuring method according to the present invention, a thickness of a film on an object surface is measured by a film thickness measuring device including a spectroscopic sensor, a memory storing theoretical values of reflectivity distribution for each film thickness and theoretical values of a characteristic variable for each film thickness and a processor. The film thickness measuring method according to the present invention includes the steps of measuring, by the spectroscopic sensor, a reflectivity distribution of the object surface with the film; and obtaining a film thickness, by the processor, based on the reflectivity distribution measured by the spectroscopic sensor using the theoretical values of reflectivity distribution for each film thickness or the theoretical values of the characteristic variable for each film thickness stored in the memory.

In the film thickness measuring method according to the present invention, a film thickness of the film of the object surface is obtained based on a reflectivity distribution measured by the spectroscopic sensor using the theoretical values of reflectivity distribution for each film thickness or the theoretical values of the characteristic variable for each film thickness. Accordingly, a film thickness can be obtained even when a wavelength corresponding to a maximum value or a minimum value does not apparently exist in the reflectivity distribution. As a result, the film thickness measuring device according to the present invention can be used for a thin film of 500 nm or less.

In the step of obtaining a film thickness of the film thickness measuring method according to an embodiment of the present invention, which is used to obtain a film thickness between the theoretical values of reflectivity distribution for each film thickness and the theoretical values of the characteristic variable for each film thickness is determined based on whether an extreme value exists in a measured reflectivity distribution curve or not and on a curvature of the curve containing the extreme value.

In the film thickness measuring method according to the present embodiment, which is used to obtain a film thickness between the theoretical values of reflectivity distribution for each film thickness and the theoretical values of the characteristic variable for each film thickness is determined based on whether an extreme value exists in a measured reflectivity distribution curve or not and on a curvature of the curve containing the extreme value. Accordingly, a film thickness of 500 nm or less can be measured in a continuous manner.

In the step of obtaining a film thickness of the film thickness measuring method according to another embodiment of the present invention, the theoretical values of the characteristic variable for each film thickness is used to determine a film thickness when an extreme value does not exist in the measured reflectivity distribution curve or the curvature of the curve containing the extreme value is too small to locate a position of the extreme value and otherwise the theoretical values of reflectivity distribution for each film thickness is used to determine a film thickness.

In the film thickness measuring method according to the present embodiment, a film thickness can be obtained using the theoretical values of reflectivity distribution even when a film thickness can not or can hardly be obtained using an extreme value in the measured reflectivity distribution curve. Further, when a film thickness can be obtained based on an extreme value in the measured reflectivity distribution curve, a film thickness is obtained using the theoretical values of reflectivity distribution, and therefore a film thickness can be uniquely determined.

In the film thickness measuring method according to another embodiment of the present invention, a measured distribution of reflectivity is used after having been corrected with such a correction coefficient as to make a measured reflectivity of a substrate without a film equal to a theoretical value.

In the film thickness measuring method according to the present embodiment, a film thickness can be measured with a higher accuracy by applying the measured reflectivity distribution to the theoretical values of reflectivity distribution.

DESCRIPTION OF THE EMBODIMENTS

Figure 1:
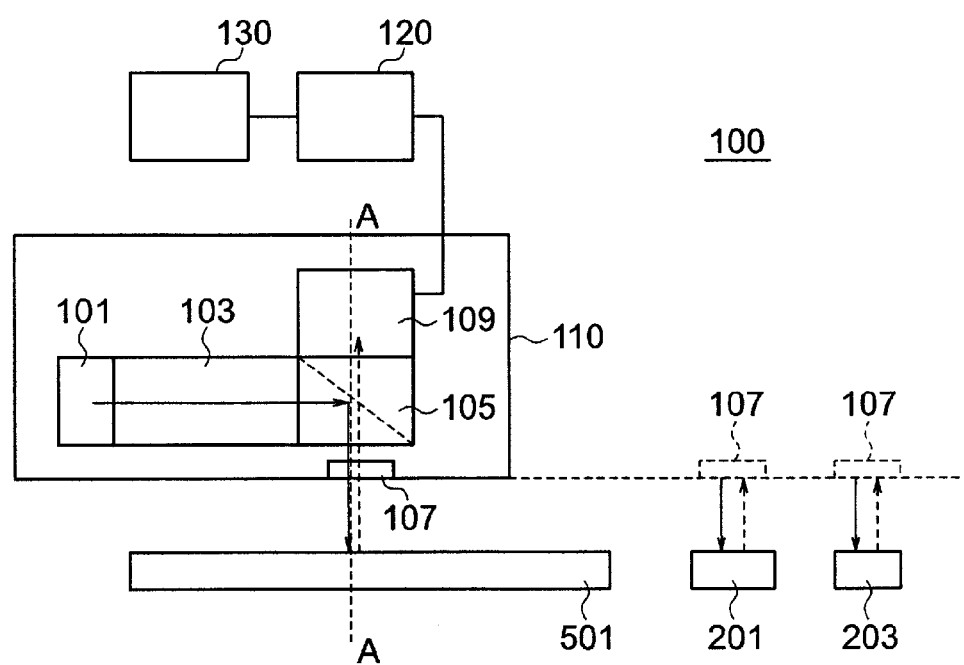
FIG. 1 shows a configuration of a film thickness measuring device according to an embodiment of the present invention.

FIG. 1 shows a configuration of a film thickness measuring device 100 according to an embodiment of the present invention. The film thickness measuring device 100 includes a measuring section 110, a processor 120 and a memory 130. The measuring section 110 includes a light emitting diode (LED) light source 101, a collimator tube 103, a beam splitter 105, a measuring window 107 and a spectral reflectivity detecting section (spectroscopic sensor) 109.

Figure 17:
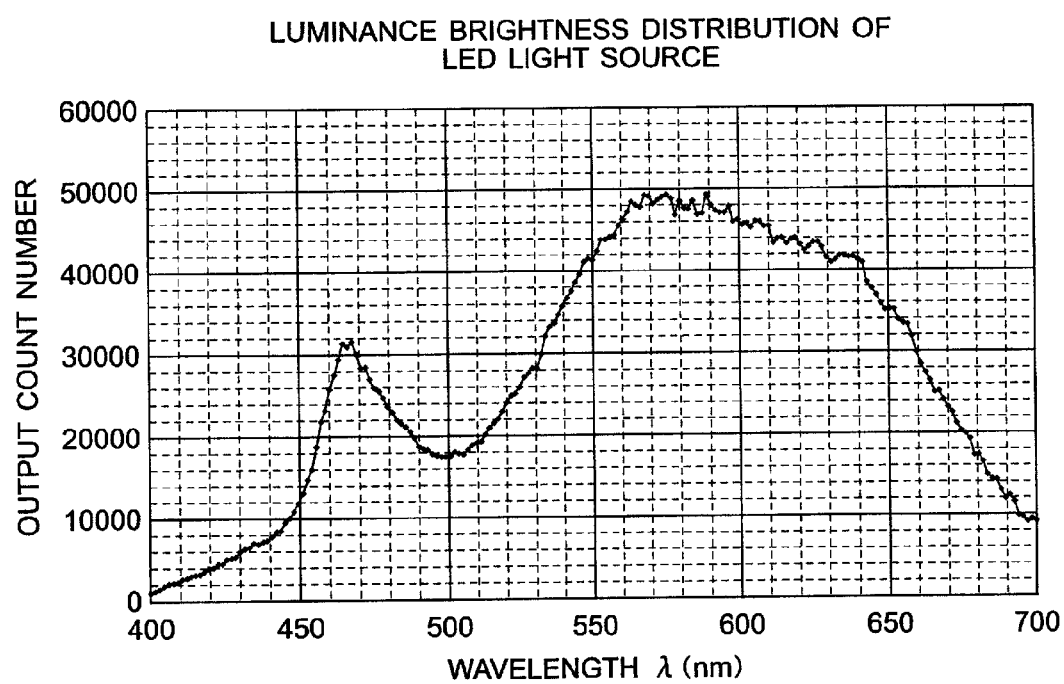
FIG. 17 shows luminance brightness of a calibration plate the specular reflection factor of which is 99% when the ultraviolet LED emitting light having the peak at 430 nm and the white color LED emitting light having the peak around 580 nm are used.

In the LED light source according to the embodiment, an ultraviolet LED emitting light having the peak at 430 nm and a white color LED emitting light having the peak around 580 nm are used. FIG. 17 shows luminance brightness of a calibration plate the specular reflection factor of which is 99% when the ultraviolet LED emitting light having the peak at 430 nm and the white color LED emitting light having the peak around 580 nm are used. As shown in FIG. 17, luminance brightness of the light source used for measurement of reflectivity is relatively high around the range from 450 nm to 500 nm. Accordingly, measuring accuracy of spectral reflectivity in the range from 400 nm to 700 nm can be improved, compared with the case in which a white color LED alone is used for the light source.

By way of example, the beam splitter 105 is a non-polarizing cube beam splitter (product code 47009-J) manufactured by Edmund optics, in which differences in transmittances and reflectivities of p polarization and s polarization are controlled within 6% in a wide range from 430 nm to 670 nm.

Light emitted from the LED light source 101 travels through the collimator tube 103, is reflected by the beam splitter 105, travels thorough the measuring window 107 and arrives at the object 501. The device is arranged such that the light illuminating the object surface is perpendicularly incident on the object surface. The light illuminating the object surface is reflected in the direction perpendicular to the object surface, travels along the path of the light illuminating the object surface in the opposite direction, arrives at the beam splitter 105, travels thorough the beam splitter 105 and arrives at the spectral reflectivity detecting section 109. In FIG. 1, the light illuminating the object surface is represented by a solid line while the light reflected by the object surface is represented by a dotted line.

In FIG. 1, the collimator tube 103 is installed on a side face of the beam splitter 105 while the spectral reflectivity detecting section 109 is installed on the top face of the beam splitter 105. In another embodiment, the collimator tube 103 and the light source may be installed on the top face of the beam splitter 105 while the spectral reflectivity detecting section 109 may be installed on a side face of the beam splitter 105.

The film thickness measuring device 100 according to the present embodiment further includes a reflectivity correcting plate 201 and a hollow member for correcting reflectivity zero point 203. Functions of the reflectivity correcting plate 201 and the hollow member for correcting reflectivity zero point 203 will be described below.

The reflectivity correcting plate 201 and the hollow member for correcting reflectivity zero point 203 are arranged such that the top faces of them are on the plane in which the top face of the object 501 is positioned. The measuring section 110 is configured such that it can move horizontally to the positions of the reflectivity correcting plate 201 and the hollow member for correcting reflectivity zero point 203 to measure reflectivities of them. Alternatively, the reflectivity correcting plate 201 and the hollow member for correcting reflectivity zero point 203 may be configured such that they can move to the position of measurement of the object 501 when it is absent.

Figure 6:
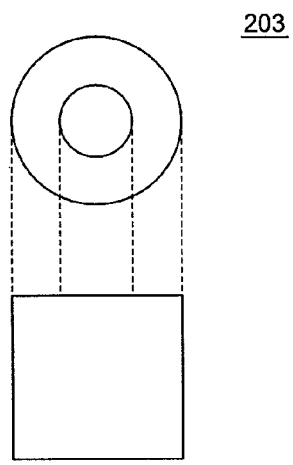
FIG. 6 shows a structure of the hollow member for correcting reflectivity zero point.

FIG. 6 shows a structure of the hollow member for correcting reflectivity zero point 203. The hollow member for correcting reflectivity zero point 203 is of a cylindrical shape. The cylinder with the bottom face has a diameter of 50 mm and a height of 50 mm. On the top face of the cylinder a circular window having a diameter of 25 mm is provided. The inside and outside surfaces of the cylinder are painted black. Reflectivity of light having entered the circular window is 0.2% or less.

The reflectivity correcting plate 201 may be a commercially available mirror of low reflectivity. For example, it may be what is referred to as product name STAN-SSL sold by Optics Inc.

Figure 7:
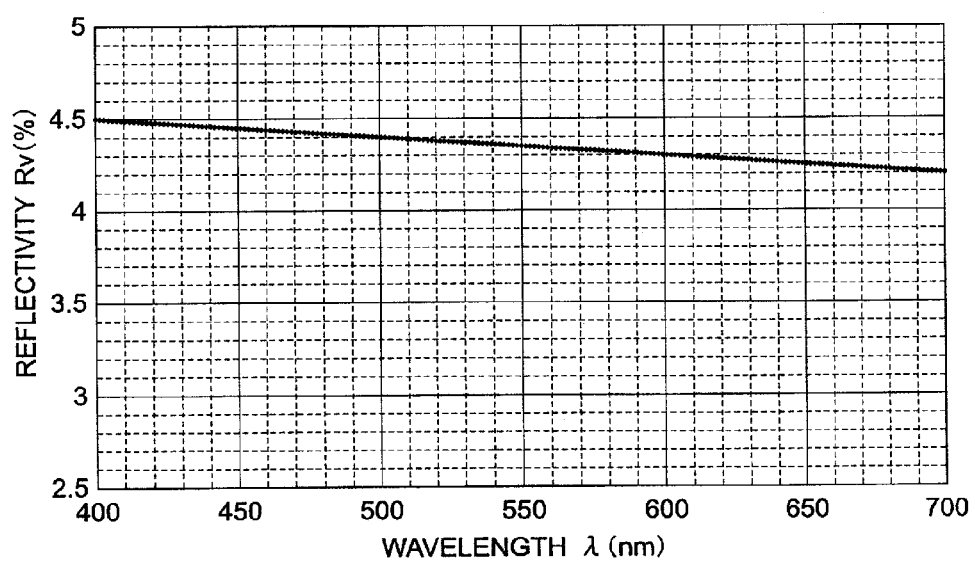
FIG. 7 shows reflectivity of the reflectivity correcting plate over wavelength.

FIG. 7 shows reflectivity of the reflectivity correcting plate 201 over wavelength.

In FIG. 1, the light entering the spectroscopic sensor 109 includes light V2 reflected by the bottom face of the beam splitter 105, light V3 which has traveled through the beam splitter 105, is reflected by the end face and further reflected by the beam splitter 105, light V4 reflected by the measuring window 107 and the like besides light V(T) reflected by the surface of the object 501.

In order to measure reflectivity of the object, it is required to remove noise such as V2, V3 and V4 besides V(T). The reflectivity correcting plate 201 and the hollow member for correcting reflectivity zero point 203 serve to remove noise such as V2, V3 and V4.

Output of the spectral reflectivity detecting section 109 which carries out measurement of reflectivity of the hollow member for correcting reflectivity zero point 203 is assumed to be V(D) while output of the spectral reflectivity detecting section 109 which carries out measurement of reflectivity of the reflectivity correcting plate 201 is assumed to be V(C). Assuming that the reflective output of the reflectivity correcting plate 201 is V(Ref), the following expression can be obtained.

$$V(C)=V(\text{Ref})+V(D)$$

Accordingly, the following expression can be obtained.

$$V(\text{Ref})=V(C)-V(D)$$

Output of the spectral reflectivity detecting section 109 which carries out measurement of reflectivity of the object surface 501 is assumed to be V(M) and the reflective output of the object surface 501 is assumed to be V(T). Then, the following expressions can be obtained.

$$V(M)=V(T)+V(D)$$

$$V(T)=V(M)-V(D)$$

Assuming that reflectivity of the reflectivity correcting plate 201 is assumed to be Rv(Ref), reflectivity of the object surface 501 can be expressed as below.

$$Rv(T)=Rv(\text{Ref})V(T)/V(\text{Ref}) \quad (1)$$

In a memory 130 of the film thickness measuring device 100, reflectivity of the reflectivity correcting plate 201 for each wavelength Rv(Ref) has been previously stored. The film thickness measuring device 100 carries out periodical measurement of V(D) and V(C) and stores the measured values in the memory 130. The film thickness measuring device 100 obtains output V(M) of the object surface 501 and obtains reflectivity of the object surface 501 for each wavelength using Rv(Ref), V(D) and V(C) and based on Expression (1). The reason why periodical measurement of V(D) and V(C) is carried out is to counter a problem of temperature drift of the output of the spectral reflectivity detecting section 109.

Figure 2:
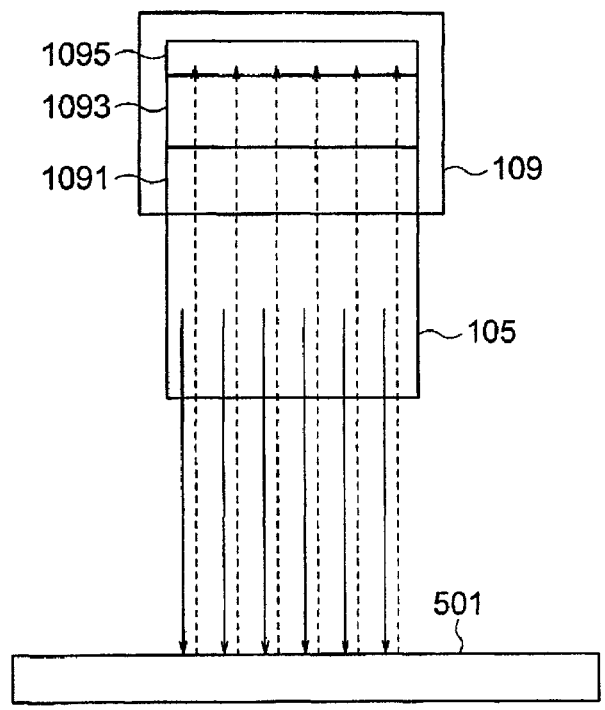
FIG. 2 shows A-A cross section of the film thickness measuring device shown in FIG. 1.

FIG. 2 shows A-A cross section of the film thickness measuring device 100 shown in FIG. 1. Light illuminating the object surface 501 is perpendicularly incident on the object surface. The light illuminating the object surface is reflected in the direction perpendicular to the object surface, travels along the path of the light illuminating the object surface in the opposite direction, arrives at the beam splitter 105, travels thorough the beam splitter 105 and arrives at the spectral reflectivity detecting section 109. The spectral reflectivity detecting section 109 is provided with a linear variable filter 1091, a collimator 1093 and an image sensor 1095. These elements will be described in detail later. In FIG. 2, the light illuminating the object 501 is represented by solid lines while the light reflected by the object 501 is represented by doted lines. The light reflected by the object 501 is perpendicularly incident on the sensor plane of the image sensor 1095 of the spectral reflectivity detecting section 109.

Figure 3:
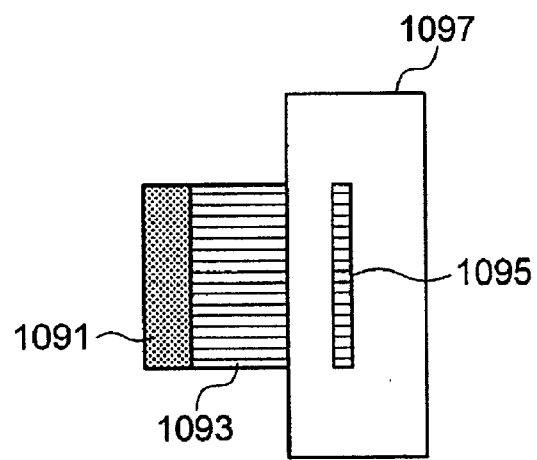
FIG. 3 shows an example of the structure of the spectral reflectivity detecting section.

FIG. 3 shows an example of the structure of the spectral reflectivity detecting section 109. As described above, the spectral reflectivity detecting section 109 is provided with a linear variable filter 1091, a collimator 1093 and an image sensor 1095. The linear variable filter 1091 is one type of interference filters in which a wavelength range of transmitted light from the shortest wavelength to the longest wavelength in the white light having entered the filter varies continuously or stepwisely depending on a position of a point on the filter thorough which the light passes.

The collimator 1093 is provided in the spectral reflectivity detecting section 109 such that a predetermined amount of clearance can be given between the linear variable filter 1091 and the image sensor 1095 and the image sensor can detect, with a high resolution, light at a wavelength which is determined by a position of a point on the linear variable filter 1091 thorough which the light passes. The reason why the predetermined amount of clearance is given between the linear variable filter 1091 and the image sensor 1095 is that multi-reflection will occur between the two elements and spectral characteristics will be deteriorated when the two elements are brought in contact with each other.

Figure 4:
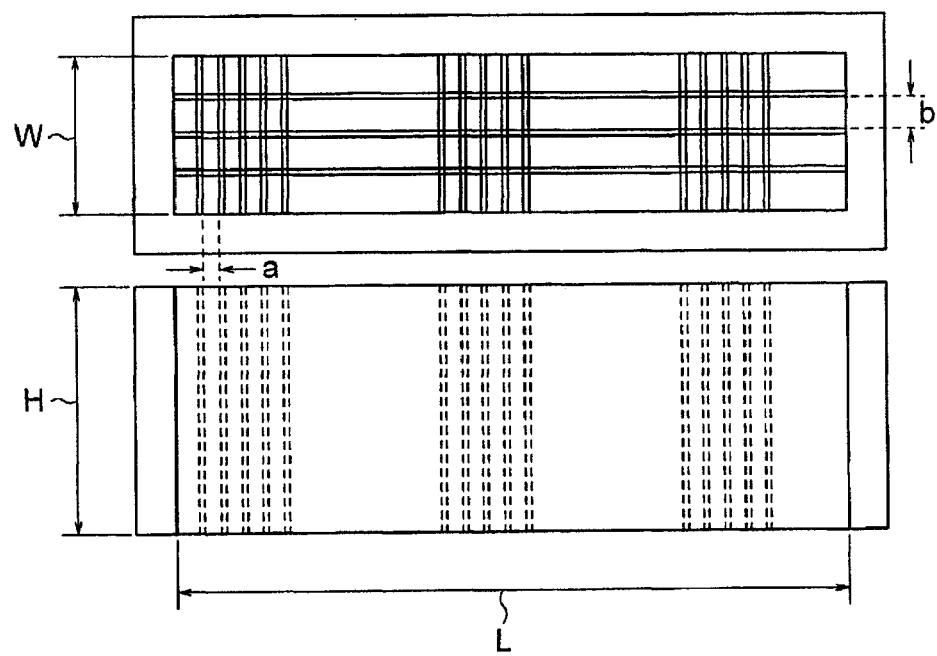
FIG. 4 shows the construction of the collimator of the spectral reflectivity detecting section.

FIG. 4 shows the construction of the collimator 1093 of the spectral reflectivity detecting section 109. By way of example, the aperture of the collimator 1093 of the spectral reflectivity detecting section 109 has width W of 2.2 mm and length L of 13 mm. Further, height H of the collimator 1093 is 1.5 mm. In FIG. 4, scale is not exact for the dimensions described above. The dimensions of the collimator 1093 are determined as below. The light receiving plane of the image sensor is a rectangle two sides of which are 2.5 mm and 12.5 mm long. On the plane, 256 photosensitive elements are arranged in the direction of L shown in FIG. 4. Two sides of each photosensitive element are 50 micrometer and 2500 micrometer long. Thus, grid interval a of the collimator 1093 is set to 40 micrometers and the repeating pitch is made equal to that of the photosensitive elements of the image sensor, 50 micrometers. To provide 256 apertures, 255 grids (SUS plates) each of which is 10 micrometer thick are provided. Grid interval b is set to 0.5 mm such that 4 apertures are provided in the aperture that is 2.2 mm wide. In FIG. 4, 3 beams each of which is 0.1 mm wide are installed in the longitudinal direction such that shapes of apertures are not deformed when being machined. Such a collimator can be produced by a method described below. The method includes steps of alternately stacking first thin metal sheets and second thin metal sheets to form a stack, the first thin metal sheets each having at least one hole formed therein; pressing the stack from both ends with a pair pressing sheets; integrating the stacked first thin metal sheets and second thin metal sheets and the pressing sheets by diffusion bonding via thermocompression; and cutting the stack along the stacking direction thereof at cutting positions corresponding to the at least one hole of each of the first thin metal sheets into the at least one collimator; wherein the stack is cut such that the at least one collimator comprises a plurality of through-holes extending therethrough that are formed by the at least one hole of each of the first thin metal sheets and that are separated from each other by the second thin metal sheets. Japanese patent 3618090 (U.S. Pat. No. 7,114,232) discloses the method in further detail. In FIG. 4, the thin metal sheets are stacked in the direction indicated by L. A collimation ratio of the collimator 1093 of the spectral reflectivity detecting section 109 is 40/1500=0.027, $$\theta=1.5°.$$

A collimation ratio is represented by a/H. A smaller collimation ratio means a higher accuracy in spectrophotometry. When the collimator height H is set to 3 mm, a collimation ratio of 0.013 is obtained. However, a required measuring time will be doubled. Accordingly, H is set to 1.5 mm from a practical standpoint.

Figure 5:
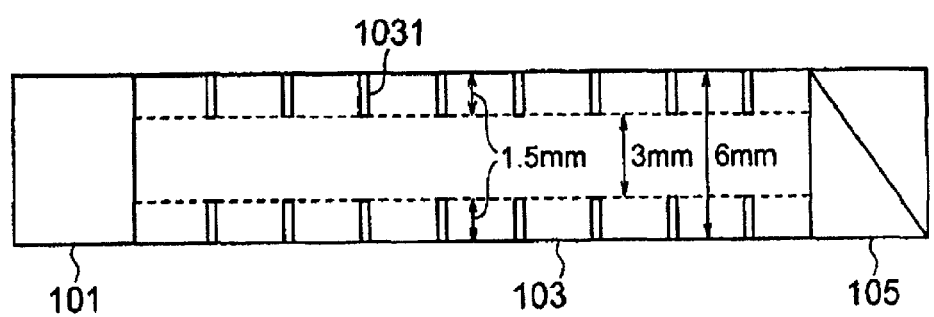
FIG. 5 shows an example of the structure of the collimator tube.

FIG. 5 shows an example of the structure of the collimator tube 103. The collimator tube 103 is 40 mm long in the longitudinal direction and a cross section perpendicular to the longitudinal direction is a rectangle having two sides which are 6 mm long and 15 mm long, respectively. The size of the rectangle is determined according to the size of the sensor plane of the image sensor 1095. The sensor plane is of a rectangle having two sides which are 2.5 mm long and 12 mm long, respectively. On the upper and lower inner surfaces of the collimator tube 103, eight traps each of which is 1.5 mm high and 15 mm wide are provided respectively. The traps prevent light diverged from the light source 101 from entering the beam splitter 105. The surfaces of the traps are coated with a matte black finish to absorb light. The collimation ratio of the collimator tube 103 is 3/40=0.075. In general, the collimation ratio of the collimator tube 103 should be 0.1 or less.

In the film thickness measuring device 100 according to the present embodiment, the beam splitter 105 is used such that light emitted by the light source can be made to be perpendicularly incident on the object surface, to be reflected by the object surface in the direction perpendicular to the object surface and to be led to the spectral reflectivity detecting section 109. The film thickness measuring device 100 according to the present embodiment has the collimator tube 103 between the light source 101 and the beam splitter 105. Accordingly, light beams emitted by the light source which travel in predetermined directions can be made to be substantially perpendicularly incident on the object surface. Further, in the film thickness measuring device 100 according to the present embodiment, the collimator of the spectral reflectivity detecting section 109 restricts the acceptance angle of photosensitive elements of the image sensor 1095 within a range which is 1.5 degrees or less. Accordingly, the image sensor 1095 can detect light beams which have been reflected by the object surface in the direction perpendicular to the object surface alone.

In the film thickness measuring device 100 according to the present embodiment, the spectral reflectivity detecting section 109 carries out measurement of reflectivity of the object surface for each wavelength, that is, a reflectivity distribution and obtains a film thickness of a film on the object surface based on the reflectivity distribution. First, reflectivity measuring function of the film thickness measuring device 100 according to the present embodiment will be described.

Figure 18:
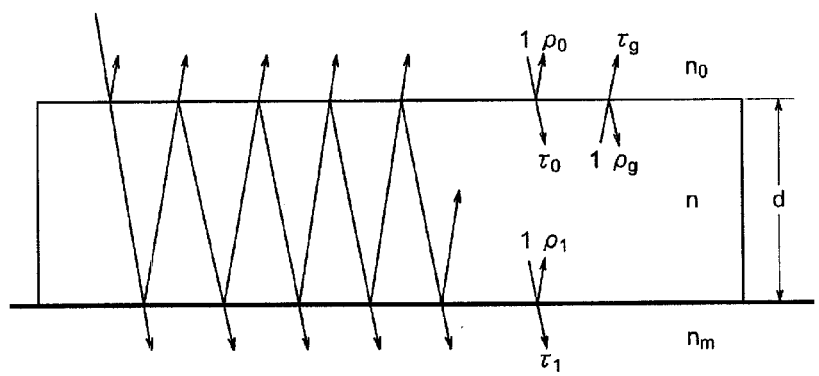
FIG. 18 schematically illustrates reflection of light on an object in which a transparent thin film (refractive index is n and film thickness is d) is formed on a substrate having a refractive index of $n_m$.

FIG. 18 schematically illustrates reflection of light on an object in which a transparent thin film (refractive index is n and film thickness is d) is formed on a substrate having a refractive index of $n_m$. A document (KOBIYAMA Mitsunobu, "Basic theory on optical thin films", published by Optronics (publisher), p 52-p 55) describes a method for obtaining spectral reflectivity as below.

Fresnel coefficients of reflection are represented as below.

$$\rho_0 = (n_0 - n)/(n_0 + n)$$

$$\rho_1 = (n - n_m)/(n + n_m)$$

$n_0$ represents a refractive index of a medium on the incident side. When the medium is air, $n_0 = 1$.

Light which has passed through the thin film of thickness d and has reached the interface between the thin film and the substrate undergoes a phase change. The phase change observed immediately before entering the substrate is represented as below.

$$\tau_0 \exp(-i\delta) = \tau_0 e^{-i\delta}$$

Assuming that $\lambda$ is the wavelength in the medium on the incident side, the following expression is obtained.

$$\delta = (2\pi n d)/\lambda$$

Reflectivity R is represented as below.

$$R = (\rho_0^2 + \rho_1^2 + 2\rho_0\rho_1 \cos 2\delta)/(1 + \rho_0^2\rho_1^2 + 2\rho_0\rho_1 \cos 2\delta) \quad (2)$$

Figure 8:
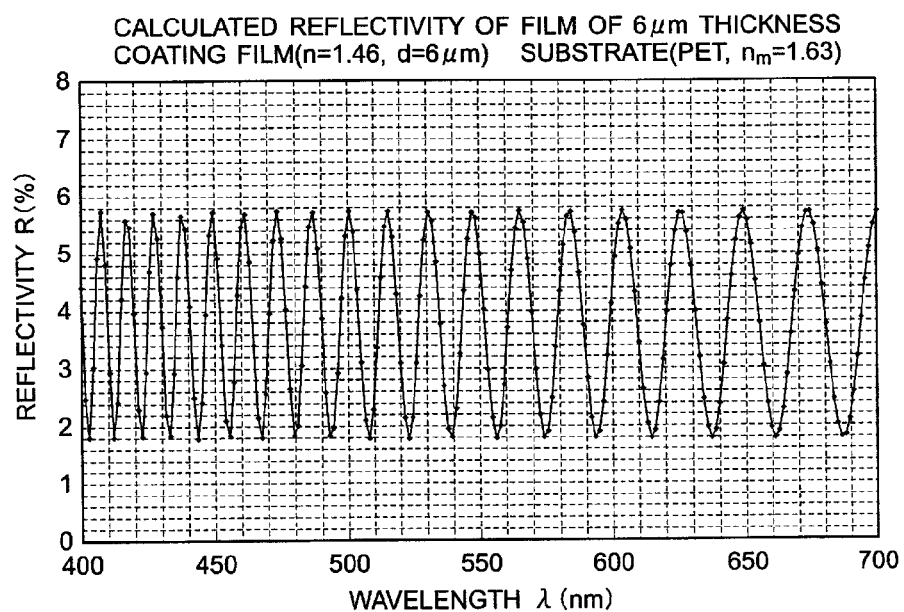
FIG. 8 shows a reflectivity distribution calculated with the assumption that the medium on the incident side is air (n=1.0) and a coating film of organic material having a refractive index n=1.46 and a film thickness of d=6 micrometers is formed on a PET (polyethylene terephthalate) substrate having a refractive index nm=1.63.

FIG. 8 shows a reflectivity distribution calculated based on Equation (2) with the assumption that the medium on the incident side is air (n=1.0) and a coating film of organic material having a refractive index n=1.46 and a film thickness of d=6 micrometers is formed on a PET (polyethylene terephthalate) substrate having a refractive index $n_m$=1.63.

Figure 9:
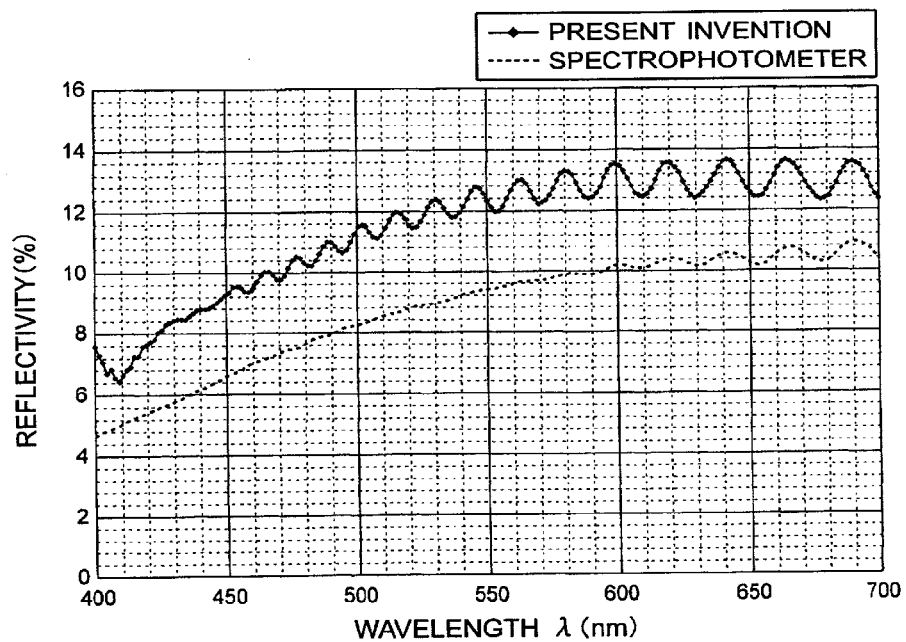
FIG. 9 shows a reflectivity distribution of the object in which a thin film is formed on a substrate obtained by measurement of the film thickness measuring device according to the present embodiment.

FIG. 9 shows a reflectivity distribution of the object in which a thin film is formed on a substrate, obtained by measurement of the film thickness measuring device according to the present embodiment. In the object, a thin film made of a transparent organic resin is applied on a substrate made of polyethylene terephthalate. The horizontal axis represents wavelength while the vertical axis represents reflectivity. In FIG. 9, the solid line represents reflectivity measured by the film thickness measuring device according to the present embodiment while the dotted line represents reflectivity measured by the spectrophotometer.

In FIG. 9, an amplitude of reflectivity change measured by the film thickness measuring device according to the present embodiment is approximately 1.2% around 680 nanometers of wavelength while an amplitude of reflectivity change measured by the spectrophotometer is approximately 0.6% around 680 nanometers of wavelength. Further, it can be clearly observed that reflectivity measured by the film thickness measuring device according to the present embodiment changes periodically in a wavelength range of 450 nanometers or more and that reflectivity measured by the spectrophotometer changes periodically in a wavelength range of 580 nanometers or more. In a wavelength range of 570 nanometers or less, a periodic change cannot be observed. The results described above clearly demonstrate that accuracy of measurement of reflectivity by the film thickness measuring device according to the present embodiment is higher than accuracy of measurement of reflectivity by the spectrophotometer.

The reason why measured reflectivity is smaller in a smaller wavelength range in FIG. 9 is supposed to lie in absorption of light by the substrate and the coating film in the smaller wavelength range. In FIG. 8, the absorption is ignored and therefore amplitude of the interference wave is constant over the whole wavelength range from 400 to 700 nanometers.

Figure 10:
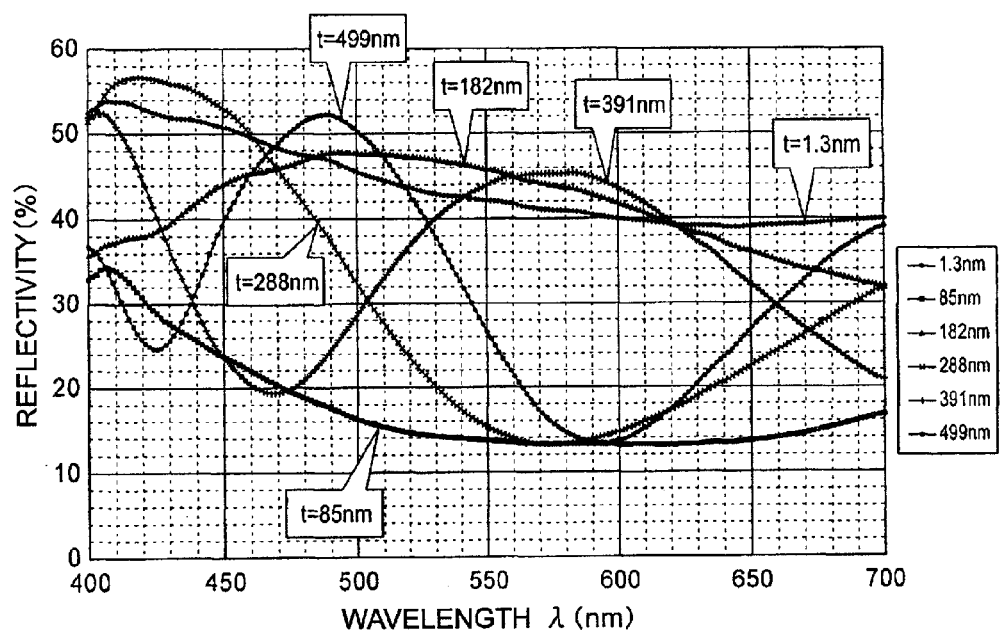
FIG. 10 shows measured reflectivity distributions of the objects in each of which an oxide film is formed on a silicon wafer.

FIG. 10 shows measured reflectivity distributions of the objects in each of which an oxide film is formed on a silicon wafer. The horizontal axis represents wavelength while the vertical axis represents reflectivity. FIG. 10 shows measured reflectivity distributions of 6 films which respectively have 6 film thicknesses from 1.3 nanometers to 499 nanometers.

In the film thickness measuring device according to the present embodiment, light illuminating the object surface is perpendicularly incident on the object surface and reflected by the object surface in the direction perpendicular to the object surface. Accordingly, the film thickness measuring device according to the present embodiment is able to carry out measurement of multi-reflection generated by the thin film a thickness of which is to be measured and thus accuracy in measurement of reflectivity can be increased. On the other hand, in the laboratory type spectrophotometer and the optical fiber type spectroreflectometer, light illuminating the object surface is not perpendicularly incident on the object surface and therefore they are not able to carry out measurement of multi-reflection generated by the thin film a thickness of which is to be measured.

Figure 11:
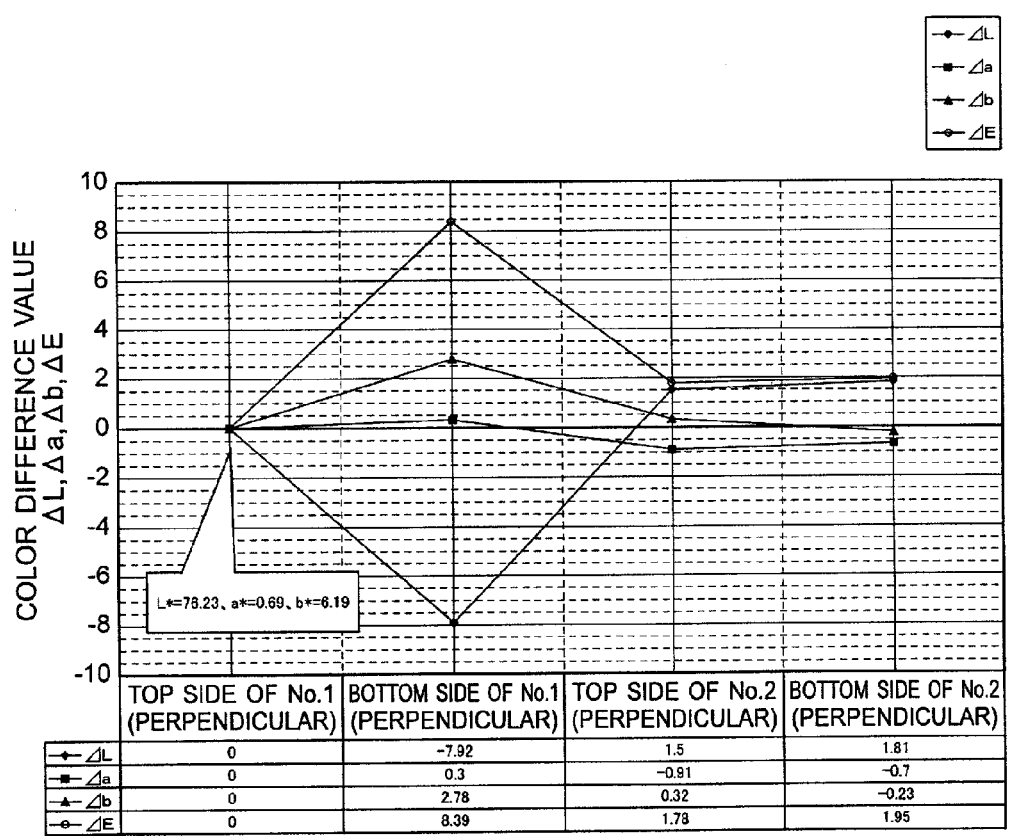
FIG. 11 shows color difference values of reflection color of 2 stainless steel sheets obtained by the film thickness measuring device according to the present embodiment.

FIG. 11 shows color difference values of reflection color of 2 stainless steel sheets, obtained by the film thickness measuring device according to the present embodiment. The horizontal axis represents kinds of objects (the top side of the first sheet, the bottom side of the first sheet, the top side of the second sheet and the bottom side of the first sheet) while the vertical axis represents color difference values. Color difference values are represented with reference to those of the object shown at the left end. L*, a* and b* represent coordinates in CIE color space. Color difference value
ΔE
is calculated by the following expression.

$$\Delta E^2 = \Delta L^2 + \Delta a^2 + \Delta b^2$$

The stainless steel sheets were arranged such that the direction of rolling traces is perpendicular to the longitudinal direction of the image sensor 1095. Rolling traces are generated in the direction of rolling when the stainless steel sheet is being rolled.

Figure 12:
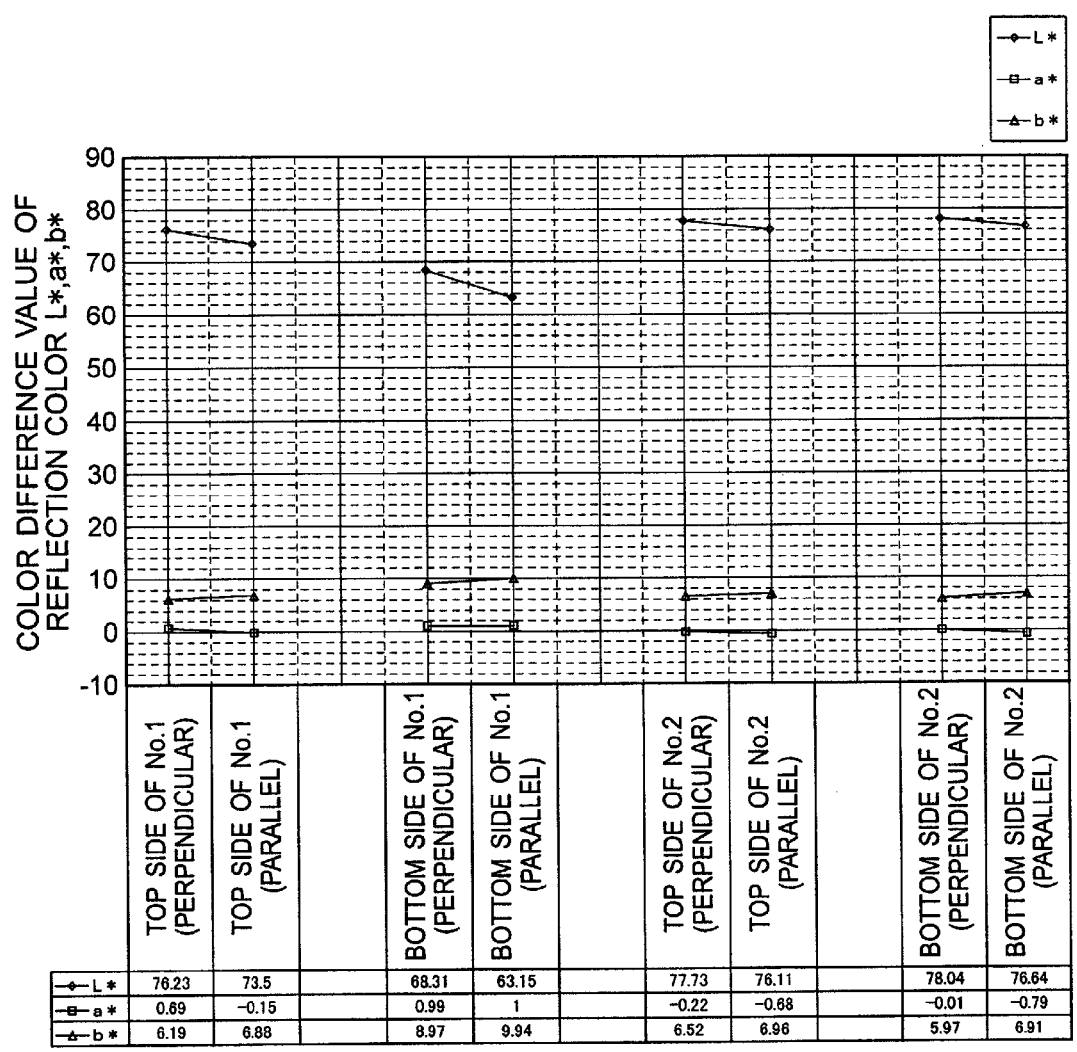
FIG. 12 shows color difference values of reflection color of 2 stainless steel sheets obtained by the film thickness measuring device according to the present embodiment.

FIG. 12 shows color difference values of reflection color of 2 stainless steel sheets, obtained by the film thickness measuring device according to the present embodiment. The horizontal axis represents kinds of objects (the top side of the first sheet, the bottom side of the first sheet, the top side of the second sheet and the bottom side of the first sheet) while the vertical axis represents color difference values. FIG. 12 shows color difference values in the case (indicated by "perpendicular" in FIG. 12) that the stainless steel sheets were arranged such that the direction of rolling traces is perpendicular to the longitudinal direction of the image sensor 1095 and those in the case (indicated by "parallel" in FIG. 12) that the stainless steel sheets were arranged such that the direction of rolling traces is parallel to the longitudinal direction of the image sensor 1095. As shown in FIG. 12, for each object, brightness value (L) is greater in the case indicated by "perpendicular" than in the case indicated by "parallel". The reason is that amount of light reflected by the sheet in the direction perpendicular to the rolling traces is greater than that reflected by the sheet in the direction parallel to the rolling traces.

Figure 13:
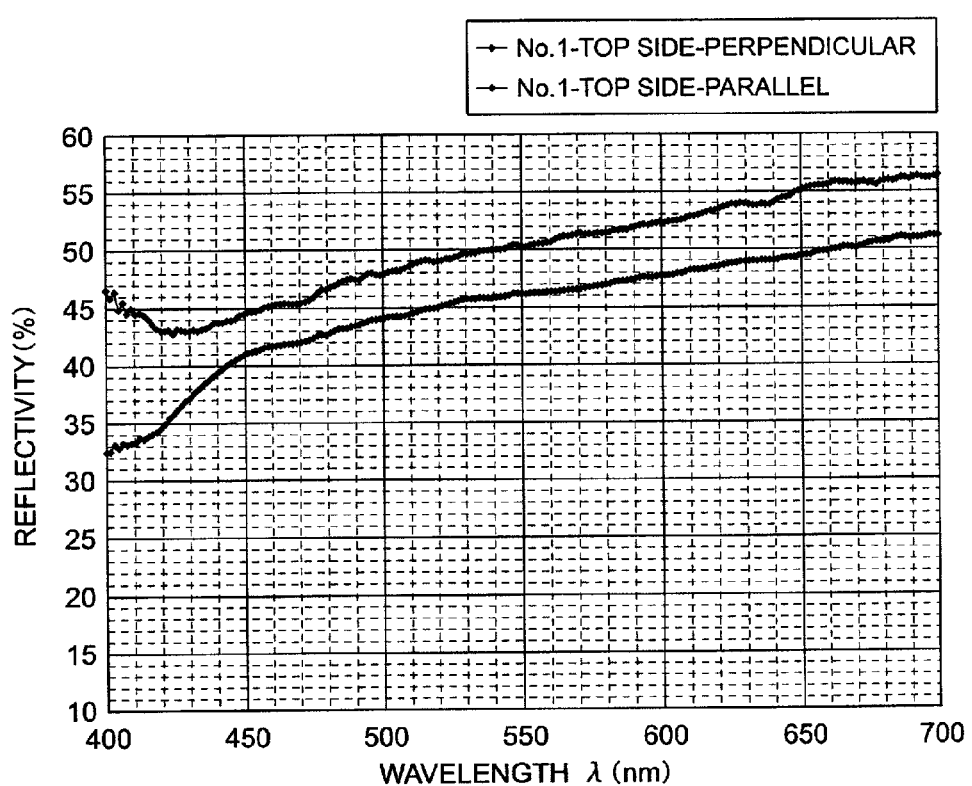
FIG. 13 shows reflectivities of a stainless steel sheet obtained by the film thickness measuring device according to the present embodiment.

FIG. 13 shows reflectivities of a stainless steel sheet obtained by the film thickness measuring device according to the present embodiment. The horizontal axis represents wavelength while the vertical axis represents reflectivity. FIG. 13 shows reflectivity in the case (indicated by "perpendicular" in FIG. 13) that the stainless steel sheet was arranged such that the direction of rolling traces is perpendicular to the longitudinal direction of the image sensor 1095 and that in the case (indicated by "parallel" in FIG. 13) that the stainless steel sheet was arranged such that the direction of rolling traces is parallel to the longitudinal direction of the image sensor 1095.

In the film thickness measuring device according to the present embodiment, light illuminating the object surface is perpendicularly incident on the object surface and reflected by the object surface in the direction perpendicular to the object surface. Accordingly, the film thickness measuring device according to the present embodiment is able to carry out measurement of reflectivity of a rough surface with rolling traces or the like.

Figure 14:
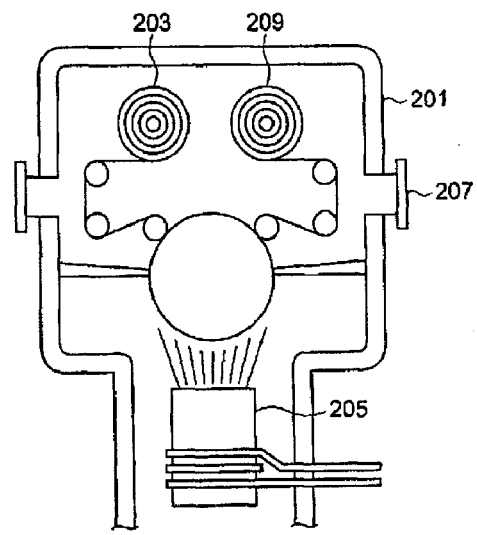
FIG. 14 shows a construction of a facility (vacuum furnace) in which a sheet is coated with a thin film.

FIG. 14 shows a construction of a facility (a vacuum furnace) in which a sheet is coated with a thin film. In the vacuum furnace 201, a coiled sheet 203 is uncoiled and a thin film is formed on the sheet through deposition by a deposition system 205. Then the sheet is coiled to generate a coiled sheet 209. The deposition system 205 carries out deposition by resistance heating, high frequency induction heating, electron beam heating or the like. A film thickness measuring device 100' which will be described below can be installed on an observing window 207.

Figure 15:
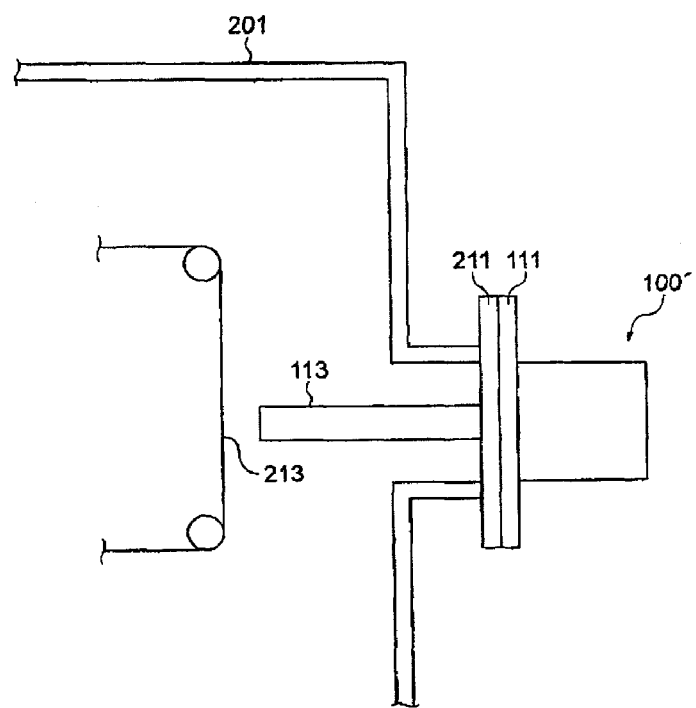
FIG. 15 shows the film thickness measuring device attached to the vacuum furnace.

FIG. 15 shows the film thickness measuring device 100' attached to the vacuum furnace 201. The film thickness measuring device 100' includes a fixing flange 111 and a light guide 113 besides the components of the film thickness measuring device 100 shown in FIG. 1. The film thickness measuring device 100' can be installed on the vacuum furnace 201 by setting the fixing flange 111 to an observing window flange 211 provided on the observing window 207 on the furnace wall of the vacuum furnace 201. By way of example, the light guide 113 is 500 mm long and its cross section perpendicular to the longitudinal direction is of a rectangular frame inner sides of which are 27 mm long and 12 mm long, respectively. A length of the light guide may be determined such that a sheet coated with a thin film which is the object is 10 mm away from the end of the light guide 113. The film thickness measuring device 100' is installed such that the longitudinal direction of the light guide 113 is perpendicular to the object surface when measurement is carried out. When the inside walls of the light guide 113 are made of material of a high reflectivity, attenuation of light passing through the light guide can be reduced. By way of example, the light guide 113 may include a tube of aluminum.

Figure 16:
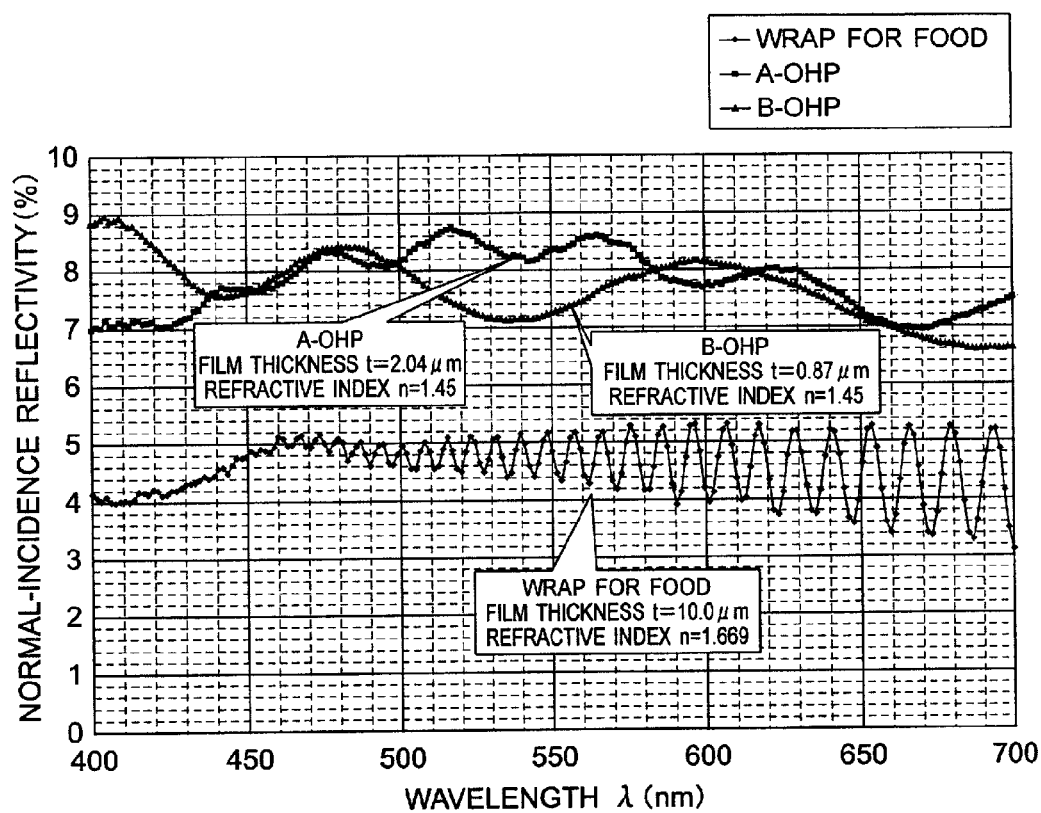
FIG. 16 shows reflectivities of objects obtained by the film thickness measuring device with a light guide.

FIG. 16 shows reflectivities of objects obtained by the film thickness measuring device 100' with the light guide 113 described above. The objects are a food wrapping film and two types of over head projector films. The film thickness measuring device 100' is installed such that the longitudinal direction of the light guide 113 is perpendicular to the object surface and a distance from the object surface to the end of the light guide 113 is 10 mm when measurement is carried out. The results are much the same as those obtained by the film thickness measuring device 100' installed such that a distance from the object surface to the end of the light guide 113 is 15 mm. Thus, a reflectivity, that is, a film thickness can be measured with a high accuracy also by the film thickness measuring device 100' with the light guide 113. Accordingly, measurement of a film thickness can be carried out in a furnace such as a vacuum surface by the film thickness measuring device 100' with the light guide 113.

A method for obtaining a film thickness from a reflectivity distribution of the object surface 501 will be described below. First, a method for obtaining a film thickness using theoretical equations will be described.

With assumed values of refractive indexes of a substrate and a film, a theoretical value (calculated value) of reflectivity for each wavelength, that is, a reflectivity distribution for a predetermined film thickness d can be obtained using Equation (2). Then, for example, a reflectivity distribution for the visible spectrum (λ=400 nm-700 nm with resolution of 1.5 nm) is obtained from Equation (2) in increments of 1 nm for film thickness d. When an extreme value of reflectivity exists over wavelength in the reflectivity distribution, the extreme value is obtained.

Figure 19:
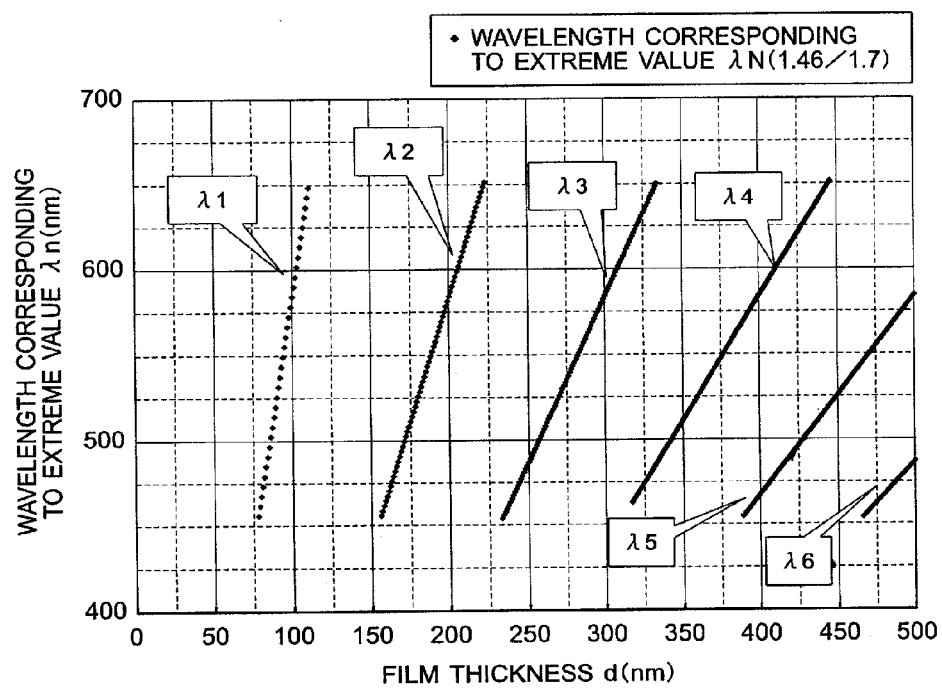
FIG. 19 represents a relationship between film thickness d and wavelength corresponding to an extreme value $\lambda M$ ($\lambda_{max}$; wavelength corresponding to a maximum value, $\lambda_{min}$; wavelength corresponding to a minimum value) when calculation is performed assuming that a refractive index of the substrate $n_m=1.7$, a refractive index of the thin film n=1.46, and a refractive index of air $n_0=1.0$.

FIG. 19 represents a relationship between film thickness d and wavelength corresponding to extreme value λM ($\lambda_{max}$; wavelength corresponding to a maximum value, $\lambda_{min}$; wavelength corresponding to a minimum value) when calculation is performed assuming that a refractive index of the substrate $n_m$=1.7, a refractive index of the thin film n=1.46, a refractive index of air $n_0$=1.0. The horizontal axis represents film thickness while the vertical axis represents wavelength corresponding to extreme value.

Between 1 nm and 77 nm, a wavelength corresponding to an extreme value does not exist and reflectivity decreases.

Wavelength λ1 corresponding to a minimum value first appears. When d=78 nm, the minimum value appears at λ1=455.5 nm and when d=111 nm, the minimum value appears at λ1=648.2 nm.

When film thickness d is between 112 nm and 155 nm, an extreme value does not exist. When d=156 nm, a maximum value appears at λ2=455.13 nm.

The wavelength corresponding to the maximum value increases with film thickness up to d=223 nm. When d=223 nm, the maximum value appears at λ2=651.16 nm.

When film thickness is between 224 nm and 232 nm, an extreme value does not exist. When film thickness d=233 nm, a minimum value appears at λ3=453.6 nm.

When film thickness d=334 nm, the minimum value appears at

λ3=650.2 nm.

When film thickness d=335 nm, the minimum value disappears.

As shown in FIG. 19, when d=317 nm, a maximum value appears at

λ4=462.87 nm.

When film thickness d is between 317 nm and 334 nm, both wavelength corresponding to a minimum value and wavelength corresponding to a maximum value exist.

Wavelength corresponding to the maximum value exists when film thickness d is between 317 nm and 446 nm and when film thickness d=446 nm, the maximum value appears at λ4=651.18 nm.

Further, when film thickness d=389 nm, a minimum value appears at

λ5=454.51 nm.

When film thickness d is between 389 nm and 446 nm, wavelength λ4 corresponding to the maximum value and wavelength λ5 corresponding to the minimum value exist. When film thickness d=500 nm, the minimum value appears at λ5=584.05 nm.

When film thickness d=467 nm, a new maximum value appears at

λ6=456.62 nm.

Thus, when film thickness d is between 447 nm and 466 nm, wavelength λ5 corresponding to the minimum value alone exists and when film thickness d is between 467 nm and 500 nm, wavelength λ5 corresponding to the minimum value and wavelength λ6 corresponding to the maximum value exist.

As seen from FIG. 19, a range of film thickness d between 1 nm and 500 nm can be divided into three kinds of rages. The first one is a range in which an extreme value does not exist. The second one is a range in which one extreme value exists. The third one is a range in which two extreme values exist. Further, wavelengths corresponding to extreme values can be divided into six groups, λ1 to λ6.

Accordingly, in order to carry out measurement of film thickness d in a range between 1 nm and 500 nm, a method by which film thickness is estimated in a range in which an extreme value does not exist and a method by which the groups of wavelength are identified and then film thickness is estimated are accordingly required.

First, a method by which film thickness is estimated in a range in which an extreme value does not exist will be described. Tristimulus values of reflection color X, Y and Z are previously obtained for each film thickness based on a reflectivity distribution for each film thickness. A measured film thickness which is determined such that a difference between the tristimulus values of reflection color and tristimulus values of reflection color obtained from a measured reflectivity distribution is minimized, is defined as a measured film thickness. The difference of tristimulus values of reflection color is defined as below.

$$\Delta W = \sqrt{(X_i - X_j)^2 + (Y_i - Y_j)^2 + (Z_i - Z_j)^2} \quad (3)$$

A method for calculating tristimulus values of reflection color is described in detail in "JIS Z8722 Methods of color measurement—Reflecting and transmitting objects". In the present embodiment, estimation of film thickness is carried out using tristimulus values X, Y and Z. Alternatively, a color value representation method based on tristimulus values of reflection color (for example, L*, a*, b*) can also be used. In the text of specification and claims, variables representing characteristics of color such as tristimulus values of reflection color, are referred to as characteristic variables.

Figure 20:
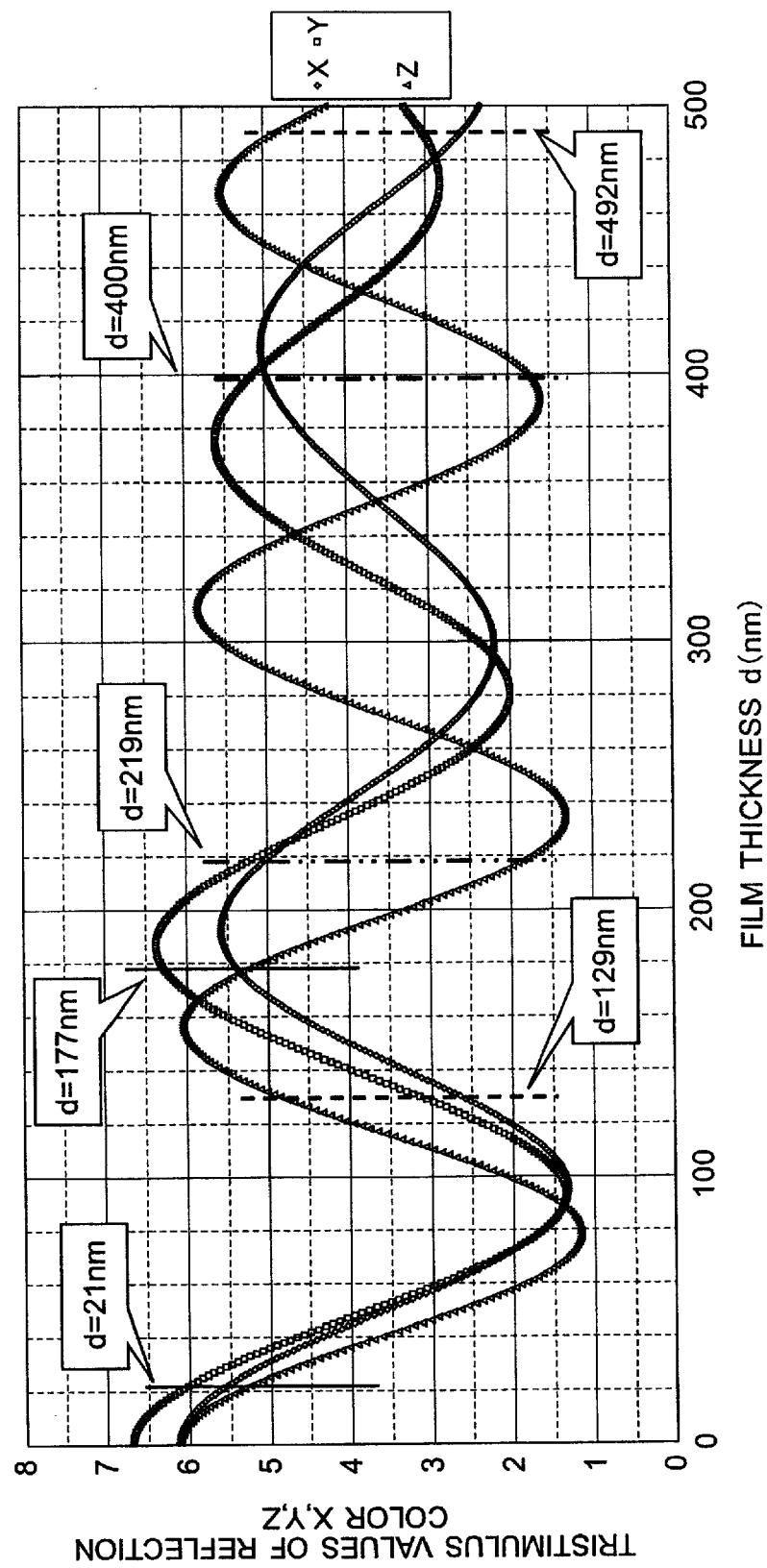
FIG. 20 shows a relationship between film thickness d and tristimulus values of reflection color X, Y and Z calculated under the same conditions as those of FIG. 19 (a refractive index of the substrate $n_m=1.7$, a refractive index of the thin film n=1.46, and a refractive index of air $n_0=1.0$)

FIG. 20 shows a relationship between film thickness d and tristimulus values of reflection color X, Y and Z calculated under the same conditions as those of FIG. 19. Refractive index of the substrate is $n_m$=1.7, refractive index of the thin film is n=1.46 and refractive index of air is $n_0$=1.0. The horizontal axis represents film thickness while the vertical axis represents tristimulus values of reflection color.

It should be noted that a phenomenon called "metamerism" in which tristimulus values are very similar even though reflectivity distributions are completely different exists. When cases in which a difference of tristimulus values ΔW shown in Equation (3) is small are searched for in FIG. 20, the following three examples are found. The first example is film thickness d=21 nm and film thickness d=177 nm. The second example is film thickness d=129 nm and film thickness d=492 nm. The third example is film thickness d=219 nm and film thickness d=400 nm.

Figure 21:
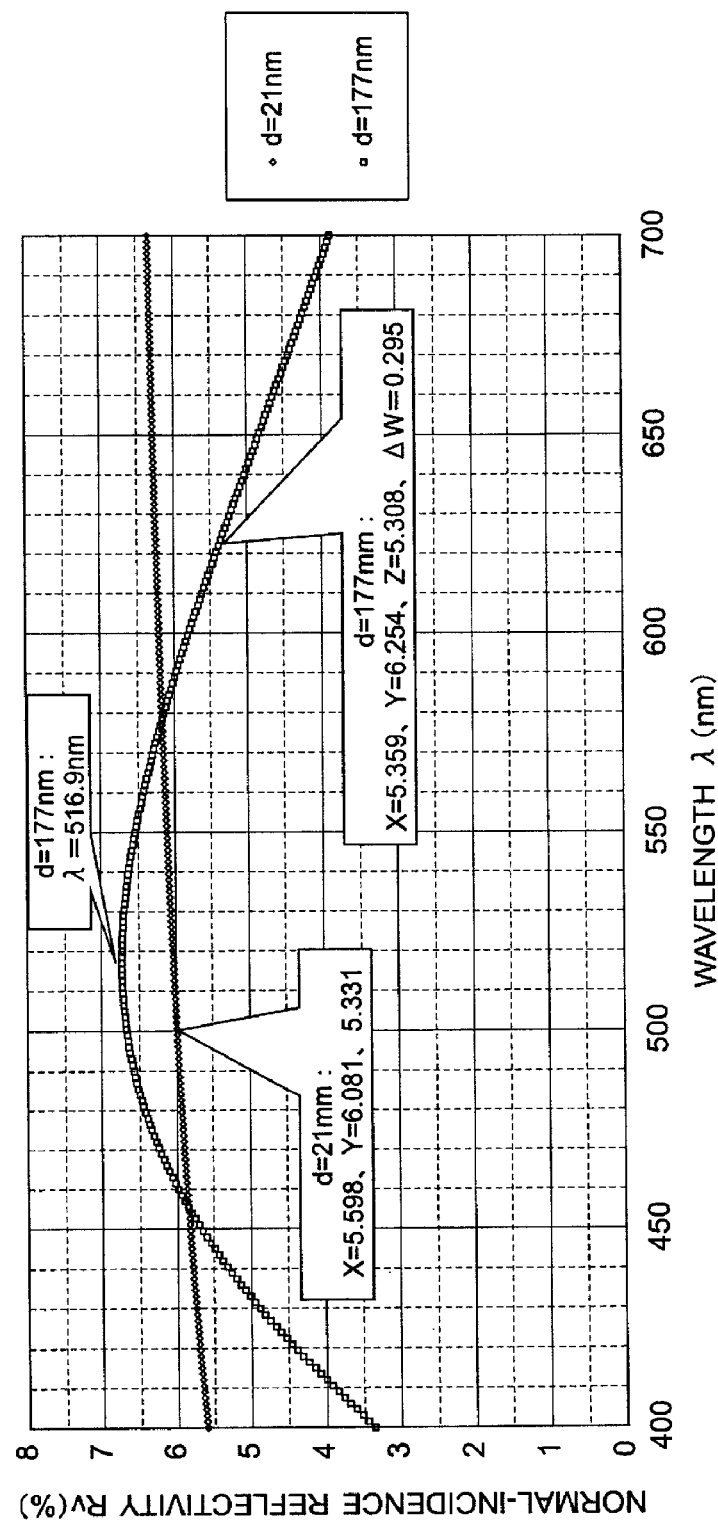
FIG. 21 shows reflectivity distributions for the first example of metamerism.

FIG. 21 shows reflectivity distributions for the first example. The horizontal axis represents wavelength while the vertical axis represents reflectivity. In the first example, an extreme value does not exist in the distribution of the thinner film thickness while one extreme value exists in the distribution of the thicker film thickness.

Figure 22:
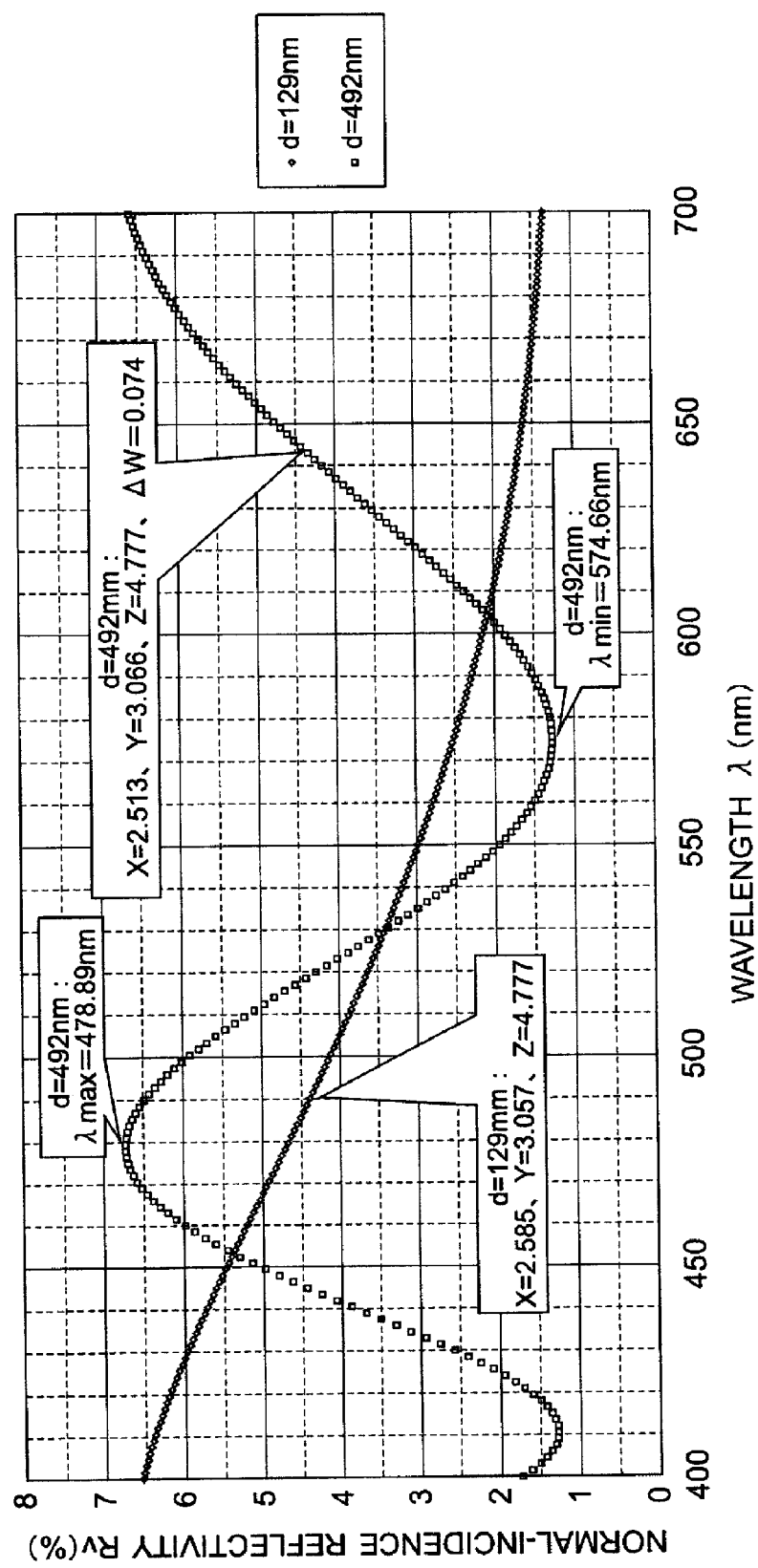
FIG. 22 shows reflectivity distributions for the second example of metamerism.

FIG. 22 shows reflectivity distributions for the second example. The horizontal axis represents wavelength while the vertical axis represents reflectivity. In the second example, an extreme value does not exist in the distribution of the thinner film thickness while two extreme values exist in the distribution of the thicker film thickness.

Figure 23:
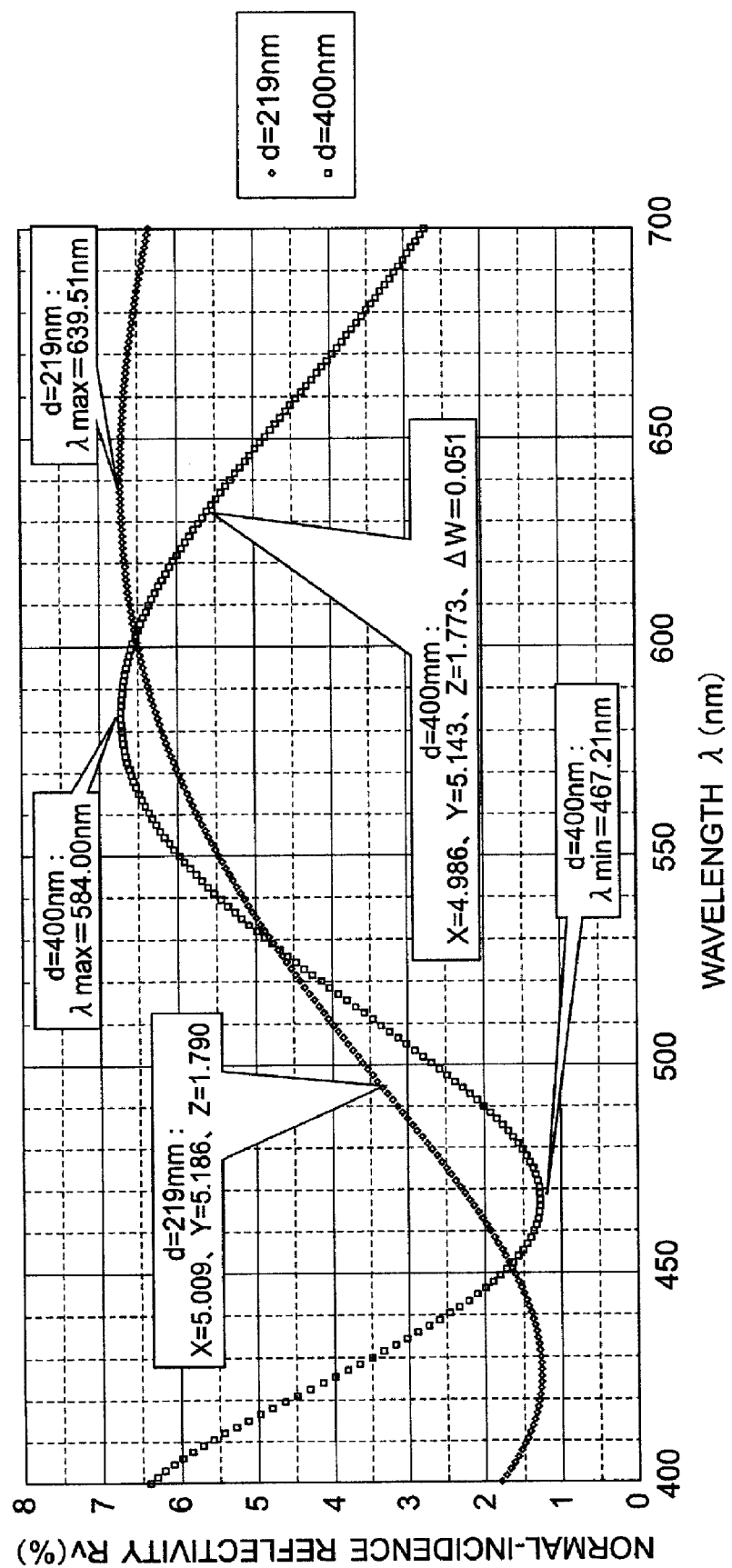
FIG. 23 shows reflectivity distributions for the third example of metamerism.

FIG. 23 shows reflectivity distributions for the third example. The horizontal axis represents wavelength while the vertical axis represents reflectivity. In the third example, one extreme value exists in the distribution of the thinner film thickness while two extreme values exist in the distribution of the thicker film thickness.

Thus, in the first to third examples, cases in which an extreme value does not exist are that with the thinner film thickness (21 nm) in the first example and that with the thinner film thickness (129 nm) in the second example. Accordingly, if film thickness is estimated based on an extreme value when it exists and film thickness is estimated based on a difference of tristimulus values of reflection color only when an extreme value does not exist, the problem of "metamerism" will not occur. That is, film thickness can be uniquely determined based on a difference of tristimulus values of reflection color.

A method by which the groups of wavelength are identified will be described below. The groups of wavelength mean λ1 to λ6 shown in FIG. 19. As described above, it has been found that in the range of film thickness from 1 nm to 500 nm, six groups of wavelength λ1 to λ6 corresponding to extreme values exist in increasing order of film thickness.

Figure 24:
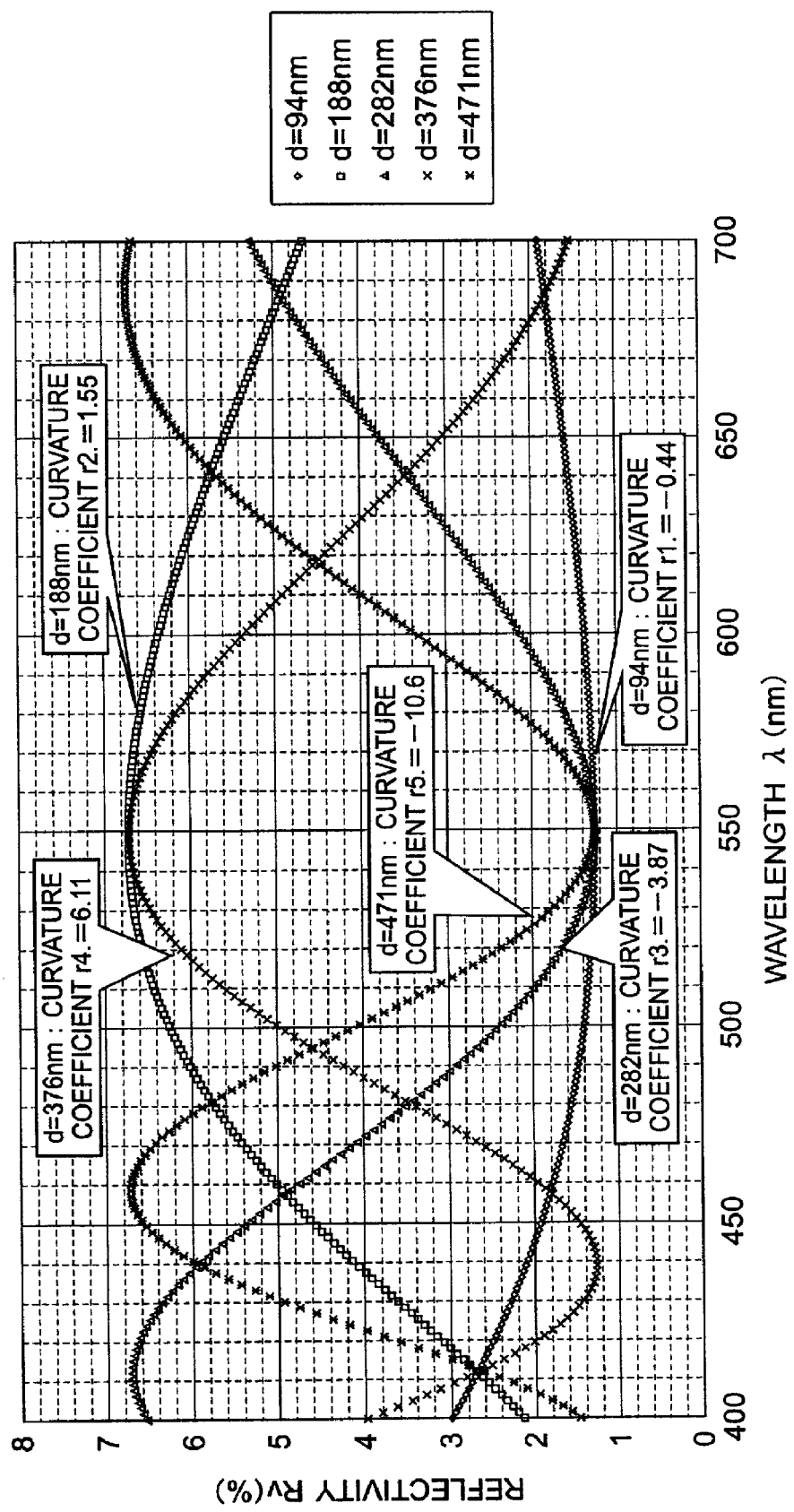
FIG. 24 shows reflectivity distributions for film thicknesses with which an extreme value of reflectivity appears at 550 nm.

FIG. 24 shows reflectivity distributions for film thicknesses with which an extreme value of reflectivity appears at 550 nm. The horizontal axis represents wavelength while the vertical axis represents reflectivity. In FIGS. 24, λ1 to λ6 correspond respectively to d=94 nm, d=188 nm, d=282 nm, d=376 nm, and d=471 nm. Hereinafter, the number which follows λ is referred to as N value. As seen from FIG. 24, curvature of the curve including an extreme value at λ=550 nm is small when N value is small and increases as N value increases. As a result, the groups of wavelength can be identified based on curvature of the curve including an extreme value.

A curvature coefficient representing an extreme value is defined as below.

$$rN = \{Rv(\lambda N-22.5\ nm) + Rv(\lambda 1+22.5\ nm) - 2Rv(\lambda N)\}/(Rv.\max - Rv.\min) \times 100$$

Rv.max=6.72(%) is the maximum reflectivity obtained by theoretical calculation ($n_m$=1.7 and n=1.46). Further, Rv.min=1.27(%) is the minimum reflectivity obtained by theoretical calculation ($n_m$=1.7 and n=1.46).

$$Rv.\max - Rv.\min = 5.45\ (\%)$$

Unit of rN is %. Wavelength difference is determined as ±22.5 nm. Alternatively, another value can be used. Further, curvature coefficient can be defined anyway provided that it represents curvature.

Curvature coefficients r1=−0.44, r2=1.55, r3=−3.87, r4=6.11 and r5=−10.6 can be obtained from FIG. 24. Negative values represent minimum values while positive values represent maximum values. Thus, based on the sign and the absolute value of a curvature coefficient a kind of an extreme value (N value) can be determined.

Figure 25:
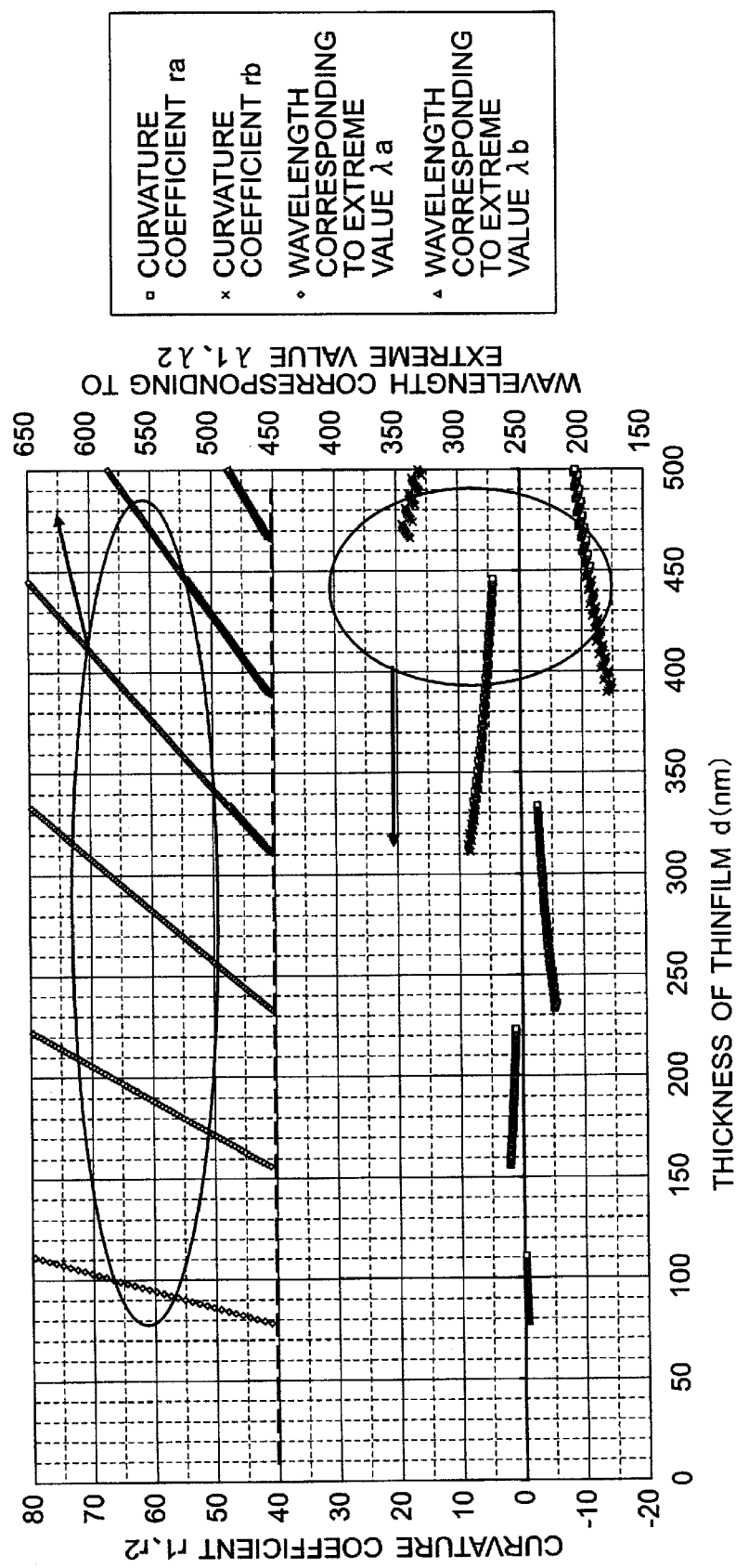
FIG. 25 shows a relationship between film thickness (d is from 1 nm to 500 nm), wavelength λN corresponding to an extreme value and curvature coefficient rN.

FIG. 25 shows a relationship between film thickness (d is from 1 nm to 500 nm), wavelength λN corresponding to an extreme value and curvature coefficient rN. The horizontal axis represents film thickness while the vertical axis represents wavelength corresponding to an extreme value (the scale on the right side) and curvature coefficient (the scale on the left side). The following findings can be obtained from FIG. 25.

In the range of film thickness d from 1 nm to 500 nm, there exist three ranges of film thickness in which an extreme value does not exist. They are a range of d from 1 nm to 78 nm, that from 112 nm to 156 nm and that from 223 nm to 234 nm.

λ1 is a minimum value and appears in a range of d from 79 nm to 111 nm. Curvature coefficient r1 is as below.

−1.0<r1<0 (%)

λ2 is a maximum value and appears in a range of d from 157 nm to 222 nm. Curvature coefficient r2 is as below.

0.86<r2<1.7 (%)

λ3 is a minimum value and appears in a range of d from 235 nm to 646 nm. Curvature coefficient r3 is as below.

−7.6<r3<−3.7 (%)

Absolute values of curvature coefficient values of extreme values for λ4 and greater N value gradually increase as N value increases.

A method for estimating film thickness based on the findings described above will be described below.

With assumed values of a refractive index (n) of the thin film and a refractive index ($n_m$) of the substrate of the object, a reflectivity distribution (a relationship between wavelength and reflectivity) and tristimulus values of reflection color are calculated and stored in a table in the memory 130. A rang of film thickness is from 1 nm to 500 nm and the resolution is 0.1 nm.

In the column of film thickness d in the above-described table, the number of wavelengths corresponding to extreme values, the wavelengths corresponding to extreme values, curvature coefficients and name of extreme value group are stored. In the case of the example shown in FIG. 25, extreme value groups are classified as below.

Group A

Group A includes ranges in which an extreme value does not exist. More specifically, Group A includes three ranges of film thickness d including that with d from 1 nm to 78 nm, that with d from 112 nm to 156 nm and that with d from 223 nm to 234 nm.

Group B

Group B includes ranges in which one extreme value exists and the curvature coefficient r is expressed as −6<r<0.25. More specifically, Group B includes three ranges of film thickness d including that with d from 78 nm to 112 nm, that with d from 156 nm to 223 nm and that with d from 234 nm to 311 nm.

Group C

Group C includes ranges in which one extreme value exists and the curvature coefficient r is expressed as 2<r or r<−7. More specifically, the former is a range with d from 334 nm to 388 nm, and the latter is a range with d from 446 nm to 466 nm.

Group D

Group D includes ranges in which two extreme values exist. More specifically, Group D includes three ranges of film thickness d including that with d from 311 nm to 334 nm, that with d from 388 nm to 446 nm and that with d from 466 nm to 500 nm.

A method for estimating film thickness using the table described above after a reflectivity distribution is measured will be described below.

Figure 32:
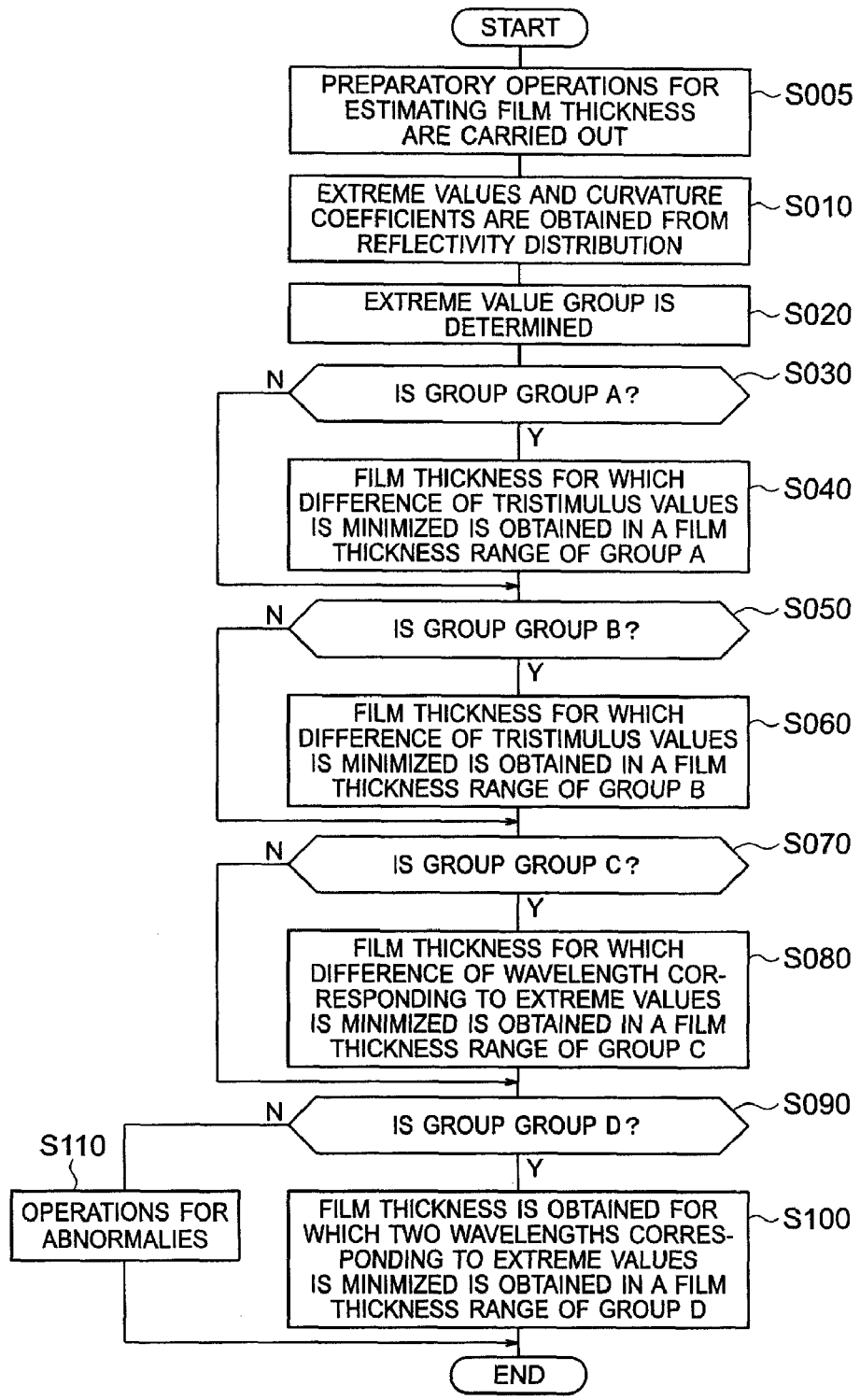
FIG. 32 is a flow chart showing a method for estimating film thickness.

FIG. 32 is a flow chart showing a method for estimating film thickness.

Each step in FIG. 32 is carried out after preparatory operations which will be described later have been carried out. By the preparatory operations, a refractive index of a film and an equation of corrected reflectivity distribution are determined. As a measured reflectivity distribution, a distribution corrected by the equation of corrected reflectivity distribution will be used.

In step S010 in FIG. 32, the processor 120 determines extreme values and their curvature coefficients from a measured reflectivity distribution. The extreme values and the curvature coefficients are referred to as measured extreme values and measured curvature coefficients.

In step S020 in FIG. 32, the processor 120 identifies extreme value groups based on the measured extreme values and the measured curvature coefficients.

In step S030 in FIG. 32, the processor 120 determines whether the extreme value group is Group A or not. If the extreme value group is Group A, the process goes to step S040. If the extreme value group is not Group A, the process goes to step S050.

In step S040 in FIG. 32, the processor 120 obtains tristimulus values of reflection color from the measured reflectivity distribution. The tristimulus values of reflection color are referred to as measured tristimulus values of reflection color. Then, the processor 120 compares tristimulus values of reflection color for each film thickness in Group A in the table stored in the memory 130, with the measured tristimulus values of reflection color, and obtains a film thickness for which a difference of tristimulus values of reflection color represented by Equation (3) is minimized.

In step S050 in FIG. 32, the processor 120 determines whether the extreme value group is Group B or not. If the extreme value group is Group B, the process goes to step S060. If the extreme value group is not Group B, the process goes to step S070.

In step S060 in FIG. 32, the processor 120 obtains tristimulus values of reflection color from the measured reflectivity distribution. The tristimulus values of reflection color are referred to as measured tristimulus values of reflection color. Then, the processor 120 compares tristimulus values of reflection color for each film thickness in Group B in the table stored in the memory 130, with the measured tristimulus values of reflection color, and obtains a film thickness for which a difference of tristimulus values of reflection color represented by Equation (3) is minimized. The reason why a film thickness is obtained using tristimulus values of reflection color and not using an existing extreme value when the extreme value group is Group B is that a curvature of the curve including the extreme value is not large enough to accurately locate a position of the extreme value.

In step S070 in FIG. 32, the processor 120 determines whether the extreme value group is Group C or not. If the extreme value group is Group C, the process goes to step S080. If the extreme value group is not Group C, the process goes to step S090.

In step S080 in FIG. 32, the processor 120 compares an extreme value for each film thickness in Group C in the table stored in the memory 130, with the measured extreme value, and obtains a film thickness for which a difference is minimized.

In step S090 in FIG. 32, the processor 120 determines whether the extreme value group is Group D or not. If the extreme value group is Group D, the process goes to step S100. If the extreme value group is not Group D, the process goes to step S110.

In step S100 in FIG. 32, the processor 120 compares (two) extreme values for each film thickness in Group D in the table stored in the memory 130, with the (two) measured extreme values, and obtains a film thickness for which differences are minimized.

In step S110 in FIG. 32, the processor 120 caries out operation for anomalies such as delivering message that "Film thickness cannot be estimated".

Figure 33:
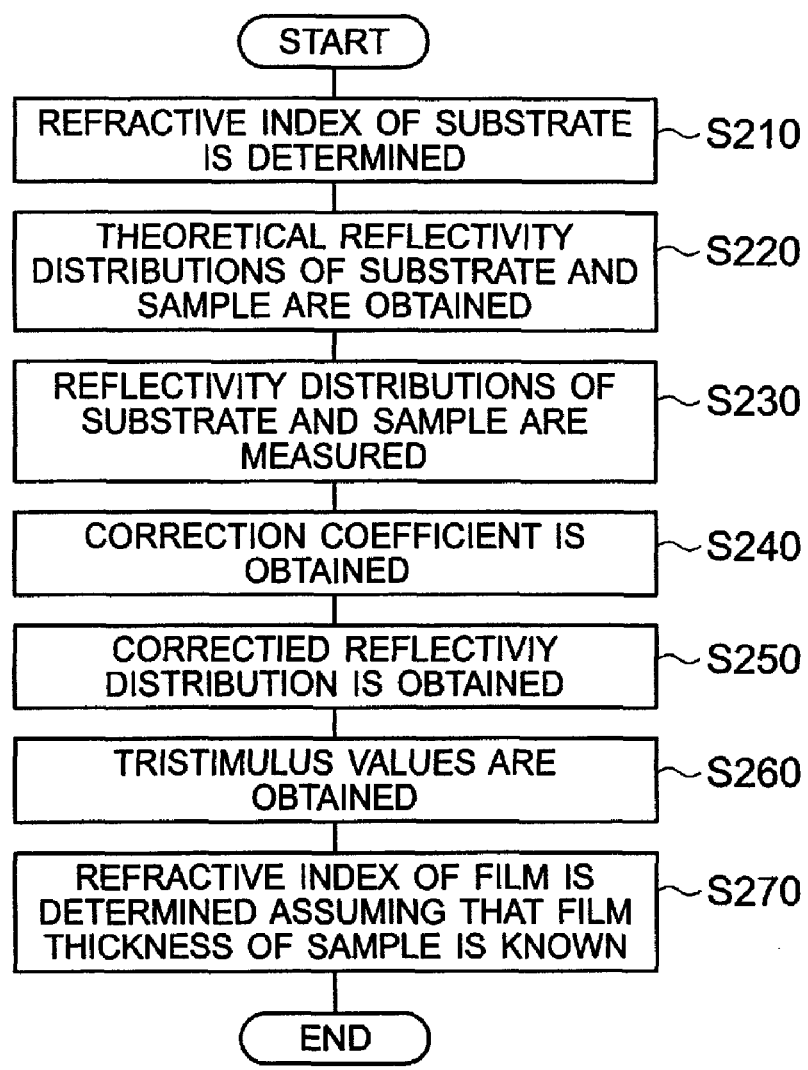
FIG. 33 is a flow chart showing preparatory operations for estimating film thickness.
Figure 34:
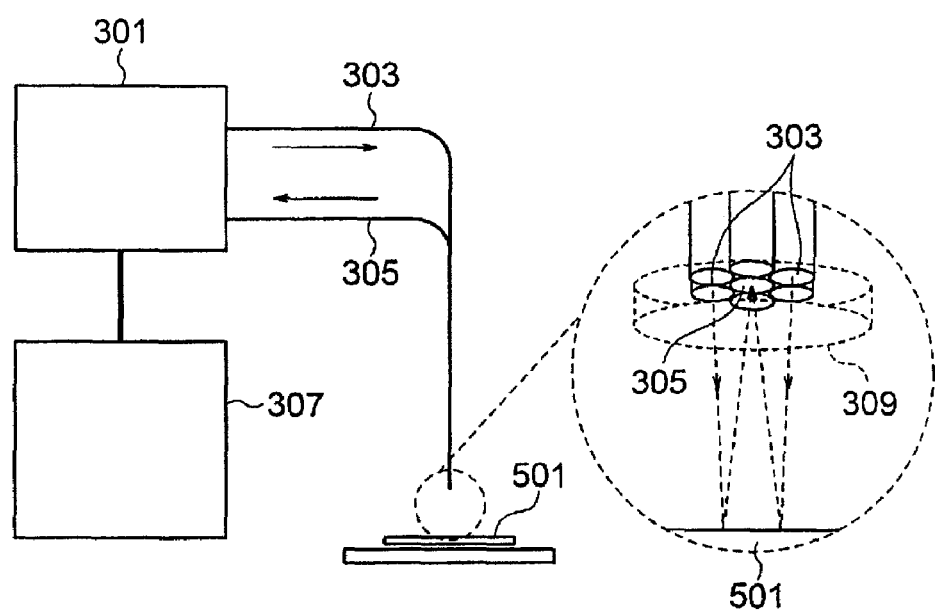
FIG. 34 shows an example of a configuration of an optical fiber type spectroreflectometer.

FIG. 33 is a flow chart showing preparatory operations for estimating film thickness. An example of a sample in which a thin film is formed on a substrate (PET) will be described.

In step S210 of FIG. 33, a refractive index of the substrate is determined.

In step S220 of FIG. 33, theoretical reflectivity distributions of the substrate and the sample are calculated.

Figure 26:
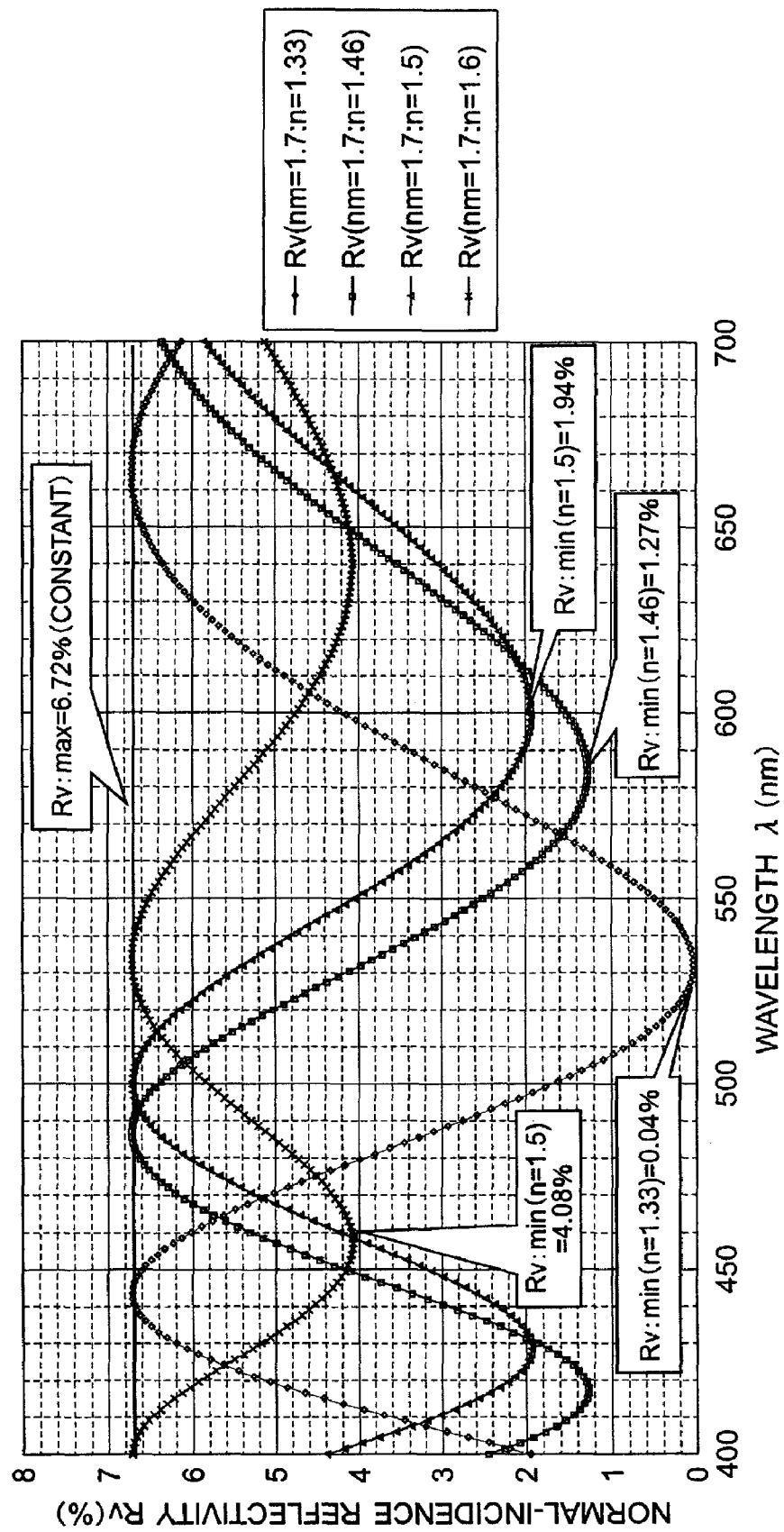
FIG. 26 shows reflectivity distributions of the case in which film thickness is 500 nm calculated using Equation (2) assuming that the refractive index of the substrate $n_m$ is 1.70 and the refractive index of the film n is 1.33, 1.46, 1.5 and 1.6.

FIG. 26 shows reflectivity distributions of the case in which film thickness is 500 nm calculated using Equation (2) assuming that the refractive index of the substrate $n_m$ is 1.70 and the refractive index of the film n is 1.33, 1.46, 1.5 and 1.6. As seen from FIG. 26, assuming that the refractive index of the substrate $n_m$ is 1.70, the maximum value of reflectivity remains unchanged and is at Rv.max=6.72%, independently of the refractive index of the thin film n. As the refractive index of the thin film n increases, the minimum value of reflectivity Rv.min increases and a difference between the maximum value and the minimum value decreases.

In step S230 of FIG. 33, reflectivity distributions of the substrate and the sample are measured.

Figure 27:
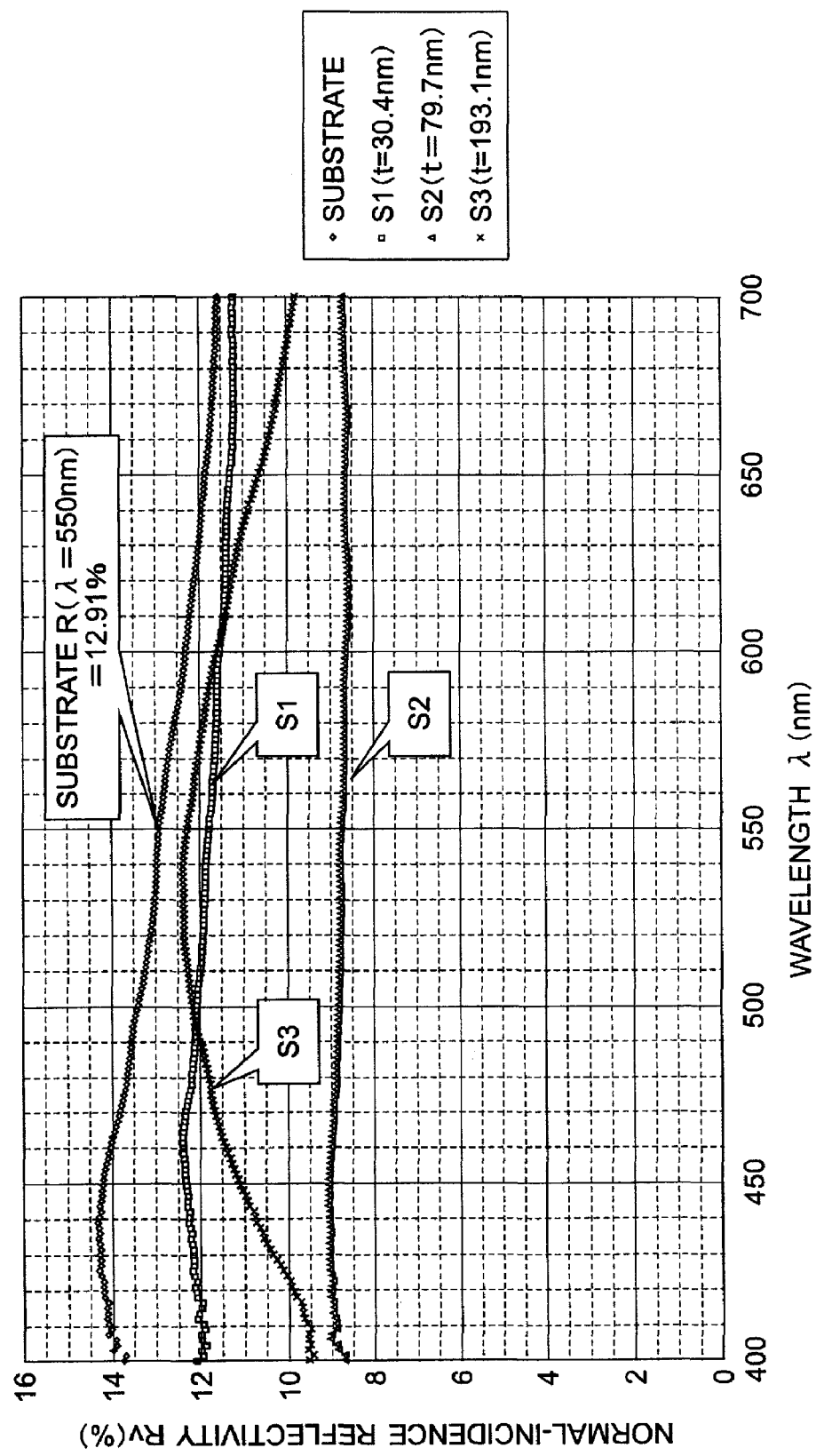
FIG. 27 shows measured reflectivity distributions of the substrate and the samples (S1, S2 and S3)

FIG. 27 shows measured reflectivity distributions of the substrate and the samples (S1, S2 and S3). The horizontal axis represents wavelength while the vertical axis represents reflectivity. Measured reflectivity distributions shown in FIG. 27 are higher than theoretical reflectivity distributions shown in FIG. 26. The reason is that in Equation (2) reflection on the bottom surface of the substrate is ignored. Further, the maximum value of theoretical reflectivity distributions shown in FIG. 26 is constant while the maximum value of measured reflectivity distributions shown in FIG. 27 is not constant. The reason is that the reflectivity has a dependence on wavelength. Accordingly, such a correction coefficient as to make the measured reflectivity of the substrate equal to the maximum value shown in FIG. 26 is required in order to apply the measured reflectivity distribution to the theoretical reflectivity distribution.

In step S240 of FIG. 33, a correction coefficient $K(\lambda)$ is obtained by the following equation.

$$K(\lambda)=Rv.t(\lambda: \max)/\{Rv((\lambda)-Rv.t(\lambda: \max)\}$$

Rv.t($\lambda$: max) is the maximum value (6.72%) shown in FIG. 26.

Figure 28:
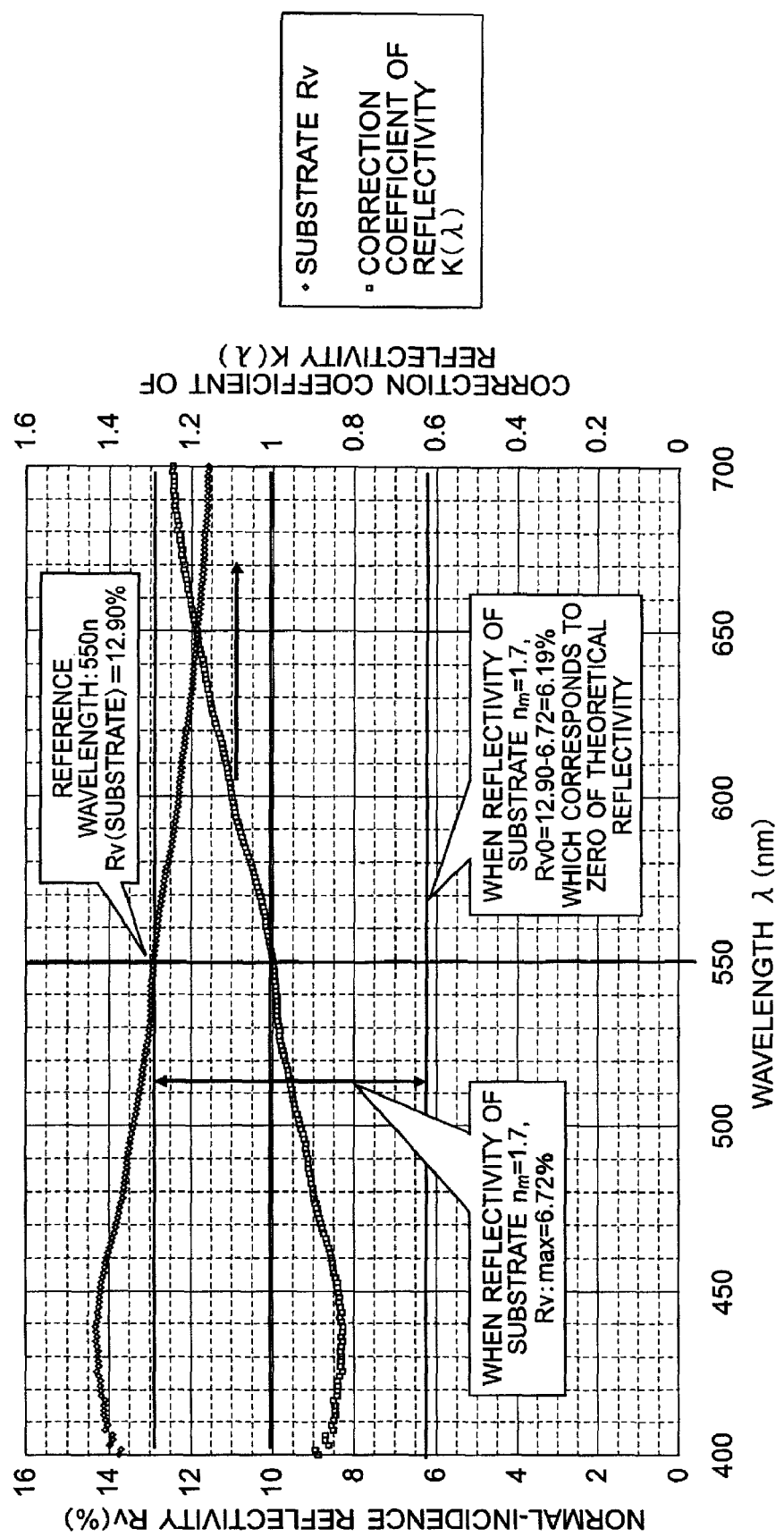
FIG. 28 shows a relationship between wavelength and correction coefficient K(λ)

FIG. 28 shows a relationship between wavelength and correction coefficient $K(\lambda)$. The horizontal axis represents wavelength while the vertical axis represents correction coefficient (scale on the right side) and reflectivity (scale on the left side).

Further, reflectivity of the bottom surface of the substrate is obtained by the following equation.

$$Rv0=Rv(550 \text{ nm})-Rv.t(\lambda: \max)=12.90-6.72=6.19(\%)$$

In step S250 of FIG. 33, a corrected reflectivity distribution $Rv^*(\lambda)$ is obtained. That is, the measured reflectivity distribution is applied to the theoretical reflectivity distribution by the following equation.

$$Rv^*(\lambda)=\{Rv(\lambda)-Rv0\} \times K(\lambda) \tag{4}$$

Figure 29:
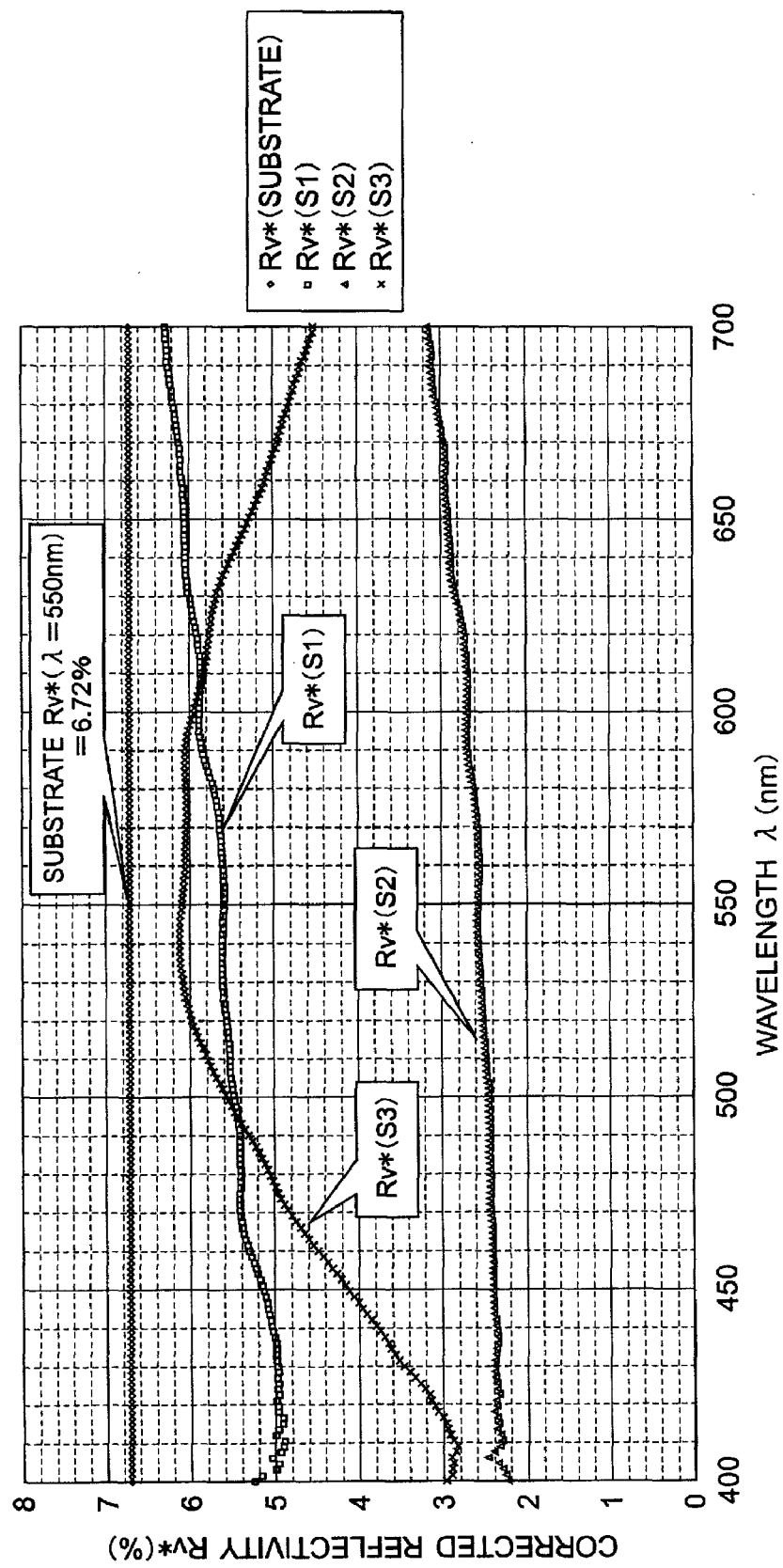
FIG. 29 shows a relationship between wavelength and corrected reflectivity distribution.

FIG. 29 shows a relationship between wavelength and corrected reflectivity distribution. The horizontal axis represents wavelength while the vertical axis represents corrected reflectivity distribution.

In step S260 of FIG. 33, tristimulus values of reflection color of the sample are obtained from the corrected reflectivity distribution of the sample.

In step S270 of FIG. 33, theoretical tristimulus values of reflection color are obtained for various refractive indexes assuming that a film thickness of the sample is known, and the refractive index of the film is determined such that a difference between the theoretical tristimulus values and the tristimulus values obtained in step S260 (Equation (3)) is minimized.

Figure 30:
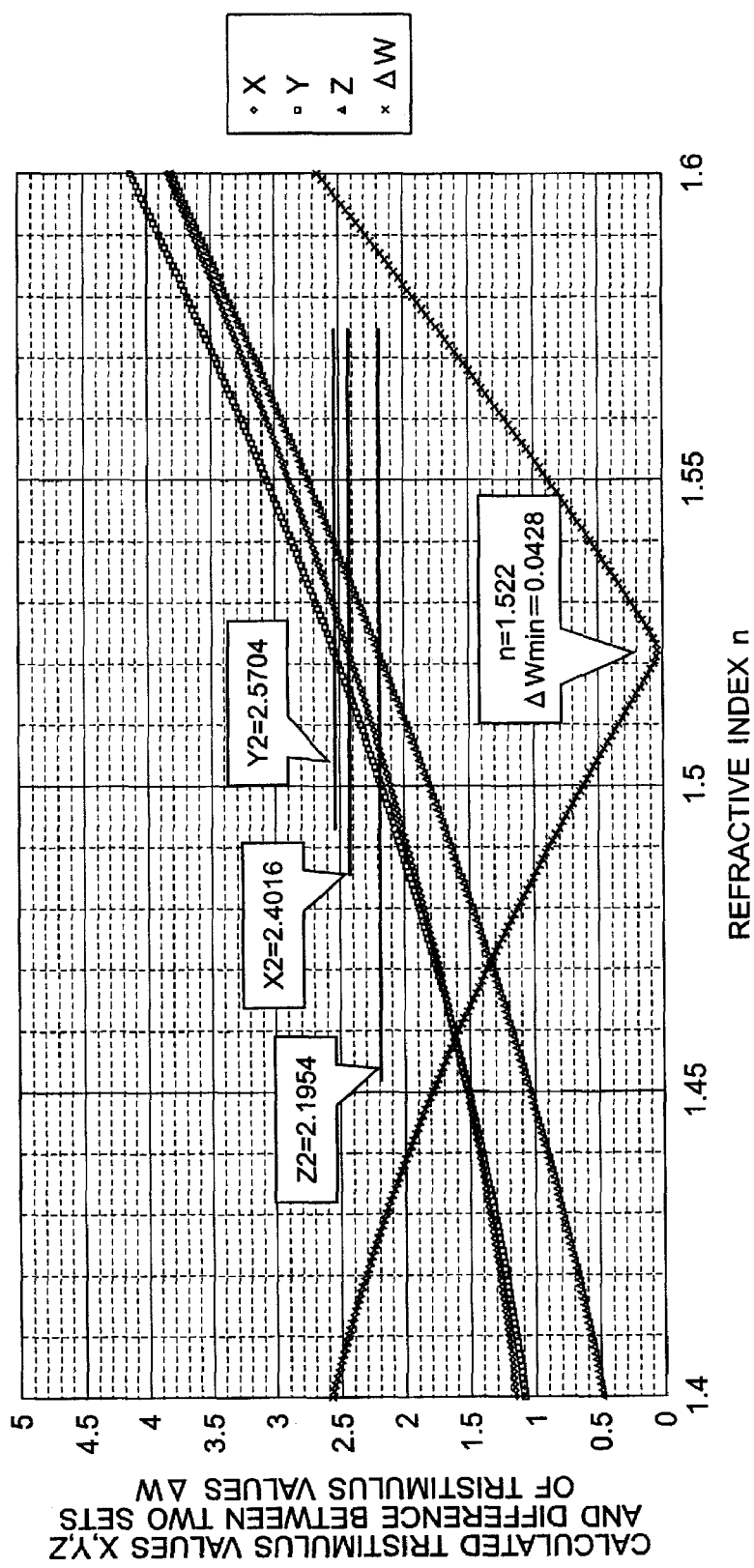
FIG. 30 shows a relationship between reflectivity of the film and theoretical tristimulus values of reflection color.

FIG. 30 shows a relationship between reflectivity of the film and theoretical tristimulus values of reflection color. The horizontal axis represents reflectivity of the film while the vertical axis represents theoretical tristimulus values of reflection color and a difference between tristimulus values of reflection color obtained from the corrected reflectivity distribution and theoretical tristimulus values of reflection color. Theoretical tristimulus values of reflection color were calculated between refractive index of the thin film n=1.26 and n=1.46 with an increment of 0.001 assuming that the film thickness is 80 nm and the reflectivity of the substrate $n_m$=1.7. Differences were obtained using Equation (3) with respect to the tristimulus values of reflection color obtained from reflectivity of sample S2, X2=2.4016, Y2=2.5704 and Z2=2.1954.

The refractive index which minimizes the difference is n=1.522.

After refractive index of the film is determined as described above, film thickness can be estimated according to the method described in FIG. 32.

Figure 31:
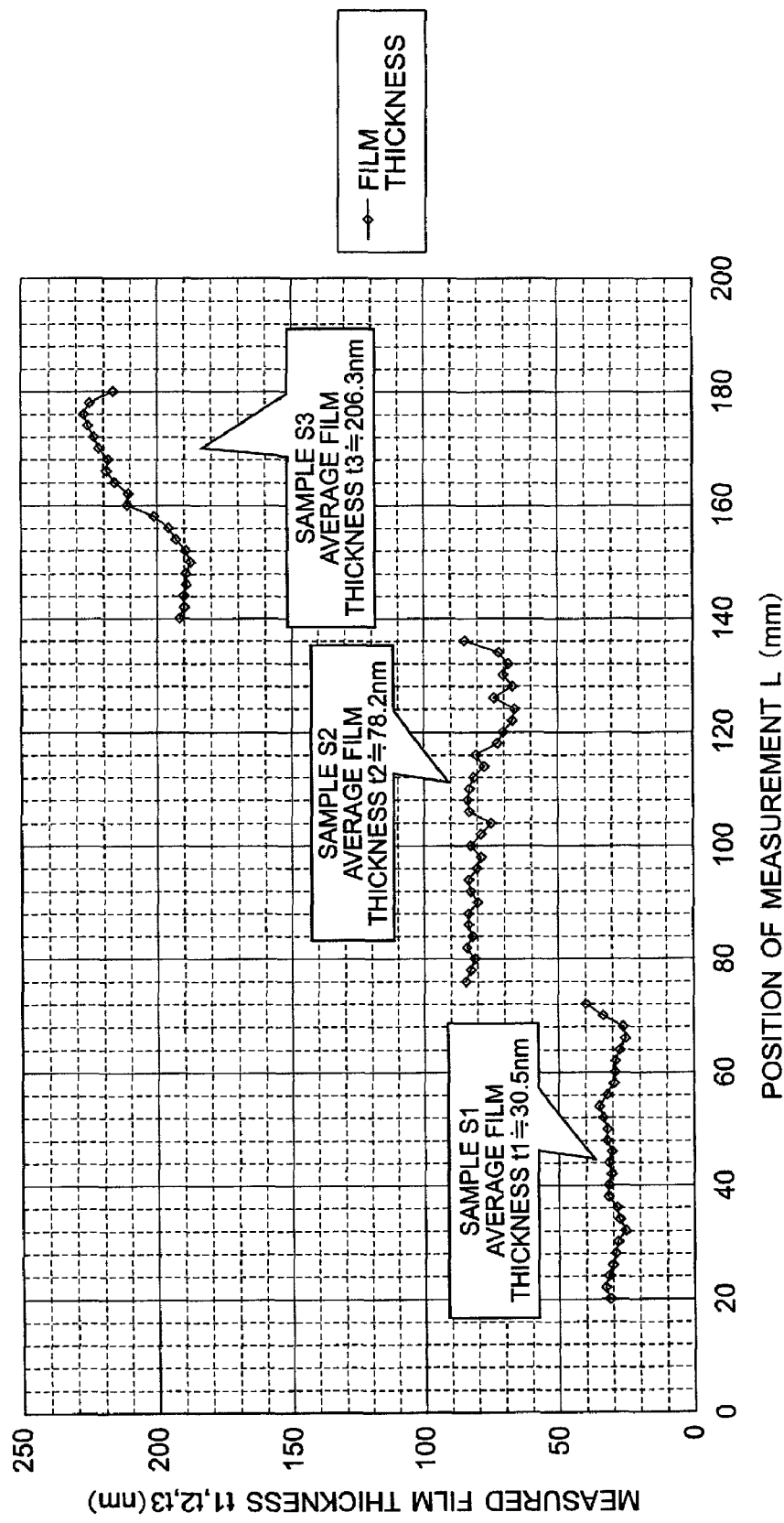
FIG. 31 shows film thickness distributions of the three samples measured by the film thickness measuring device according to the present embodiment.

FIG. 31 shows film thickness distributions of the three samples measured by the film thickness measuring device according to the present embodiment. The horizontal axis represents position of measurement while the vertical axis represents measured film thickness. The average film thicknesses of samples S1, S2 and S3 are 30.5 nm, 78.2 nm and 206.3 nm, respectively. These values are reasonable.

In the method shown in FIG. 33, a thin film was on a transparent substrate. The method can be similarly applicable to the case in which a thin film is on an opaque substrate such as Si wafers or metals.

What is claimed is:

1. A film thickness measuring device comprising a light source, a spectroscopic sensor, a processor, and a memory,
    wherein the device is configured such that light from the light source is perpendicularly incident on an object surface with a film and light reflected by the object surface is led to enter the spectroscopic sensor, and
    wherein the memory stores theoretical values of a characteristic variable representing characteristics of color for each film thickness, and
    wherein the processor is configured to obtain a film thickness of the film of the object surface based on a reflectivity distribution measured by the spectroscopic sensor using the theoretical values of the characteristic variable representing characteristics of color for each film thickness stored in the memory.

2. A film thickness measuring device according to claim 1, wherein the device further comprises a beam splitter and the device is configured such that during a measurement period, light from the light source passes through the beam splitter and is perpendicularly incident on the object surface and light reflected by the object surface travels in a direction perpendicular to the object surface, passes through the beam splitter and reaches the spectroscopic sensor.

3. A film thickness measuring device according to claim 2, wherein the device further comprises a hollow member for correcting reflectivity zero point with an aperture and a reflectivity correcting plate and the device is configured such that during a period for correcting reflectivity zero point, light from the light source passes through the beam splitter and enters the aperture of the hollow member for correcting reflectivity zero point and light reflected by the hollow member travels in a direction perpendicular to the object surface, passes through the beam splitter and reaches the spectroscopic sensor, and
    wherein the device is configured such that during a period for calibrating reflectivity, light from the light source passes through the beam splitter and is perpendicularly incident on the reflectivity correcting plate and light reflected by the reflectivity correcting plate travels in a direction perpendicular to the reflectivity correcting plate, passes through the beam splitter and reaches the spectroscopic sensor, and
    wherein the memory stores reflectivity of the reflectivity correcting plate Rv(Ref) and the processor obtains reflectivity of the object surface Rv(T) using equation $$Rv(T)=Rv(\text{Ref})\cdot(V(M)-V(D))/(V(C)-V(D))$$

where V(M) represents output of the spectroscopic sensor during the measurement period, V(D) represents output of the spectroscopic sensor during the period for correcting reflectivity zero point, and V(C) represents output of the spectroscopic sensor during the period for calibrating reflectivity.

4. A film thickness measuring method by which a thickness of a film on an object surface is measured by a film thickness measuring device including a spectroscopic sensor, a memory storing theoretical values of a characteristic variable representing characteristics of color for each film thickness and a processor, the method comprising the steps of:
    measuring, by the spectroscopic sensor, a reflectivity distribution of the object surface with the film; and
    obtaining a film thickness, by the processor, based on the reflectivity distribution measured by the spectroscopic sensor using the theoretical values of the characteristic variable representing characteristics of color for each film thickness stored in the memory.

5. A film thickness measuring method according to claim 4, wherein in the step of obtaining a film thickness, which is used to obtain a film thickness between the theoretical values of reflectivity distribution for each film thickness and the theoretical values of the characteristic variable for each film thickness is determined based on whether an extreme value exists in a measured reflectivity distribution curve or not and on a curvature of the curve containing the extreme value.

6. A film thickness measuring method according to claim 5, wherein in the step of obtaining a film thickness, the theoretical values of the characteristic variable for each film thickness is used to determine a film thickness when an extreme value does not exist in the measured reflectivity distribution curve or the curvature of the curve containing the extreme value is too small to locate a position of the extreme value and otherwise the theoretical values of reflectivity distribution for each film thickness is used to determine a film thickness.

7. A film thickness measuring method according to claim 4, wherein a measured distribution of reflectivity is used after having been corrected with such a correction coefficient as to make a measured reflectivity of a substrate without a film equal to a theoretical value.

* * * * *